(12) United States Patent
Noguchi

(10) Patent No.: US 11,576,646 B2
(45) Date of Patent: Feb. 14, 2023

(54) ULTRASOUND DIAGNOSTIC APPARATUS AND METHOD FOR CONTROLLING ULTRASOUND DIAGNOSTIC APPARATUS

(71) Applicant: FUJIFILM Corporation, Tokyo (JP)

(72) Inventor: Masafumi Noguchi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 669 days.

(21) Appl. No.: 16/586,426

(22) Filed: Sep. 27, 2019

(65) Prior Publication Data
US 2020/0022671 A1    Jan. 23, 2020

Related U.S. Application Data

(63) Continuation of application No. PCT/JP2018/012035, filed on Mar. 26, 2018.

(30) Foreign Application Priority Data

Mar. 30, 2017    (JP) .............................. JP2017-067548

(51) Int. Cl.
     *A61B 8/06*          (2006.01)
     *A61B 8/08*          (2006.01)

(52) U.S. Cl.
     CPC ................ *A61B 8/06* (2013.01); *A61B 8/488* (2013.01); *A61B 8/5276* (2013.01)

(58) Field of Classification Search
     CPC ......... A61B 8/06; A61B 8/488; A61B 8/5276; G01S 15/8981
     See application file for complete search history.

(56) References Cited

U.S. PATENT DOCUMENTS

2013/0281846 A1   10/2013   Yoshiara et al.
2015/0320395 A1   11/2015   Sato

FOREIGN PATENT DOCUMENTS

EP          0524774 A2     1/1993
JP          63-59938 A     3/1988
(Continued)

OTHER PUBLICATIONS

International Preliminary Report on Patentability and Written Opinion of the International Searching Authority(Forms PCT/IB/326, PCT/IB/373 and PCT/ISA/237), dated Oct. 10, 2019, for International Application No. PCT/JP2018/012035, with an English Translation.

(Continued)

*Primary Examiner* — Boniface Ngathi N
(74) *Attorney, Agent, or Firm* — Birch, Stewart, Kolasch & Birch, LLP

(57) ABSTRACT

An ultrasound diagnostic apparatus 1 includes: a data acquisition unit 3 that repeatedly transmits an ultrasound beam to a subject a plurality of times in a range over a plurality of scanning lines to acquire a time-series data string of reflected waves from the subject; an analysis target data selection unit 7 that estimates the amount of relative positional deviation of a scatterer of the subject which is included in the time-series data string and excludes time-series data satisfying an exclusion condition based on the amount of positional deviation of the scatterer from the time-series data string to select analysis target data; an MTI filter unit 8 that removes a clutter component from the analysis target data; and a blood flow information estimation unit 9 that analyzes the analysis target data from which the clutter component has been removed to estimate blood flow information of the subject.

20 Claims, 15 Drawing Sheets

(56) References Cited

FOREIGN PATENT DOCUMENTS

| | | |
|---|---|---|
| JP | 5-192336 A | 8/1993 |
| JP | 7-328001 A | 12/1995 |
| JP | 9-220228 A | 8/1997 |
| JP | 2004-73672 A | 3/2004 |
| JP | 2014-158698 A | 9/2014 |
| JP | 2018-33670 A | 3/2018 |

OTHER PUBLICATIONS

International Search Report (PCT/ISA/210), dated May 22, 2018, for International Application No. PCT/JP2018/012035, with an English translation.
Extended European Search Report for corresponding European Application No. 18776937.7, dated Mar. 17, 2020.

ULTRASOUND DIAGNOSTIC APPARATUS AND METHOD FOR CONTROLLING ULTRASOUND DIAGNOSTIC APPARATUS

CROSS-REFERENCE TO RELATED APPLICATIONS

This application is a Continuation of PCT International Application No. PCT/JP2018/012035 filed on Mar. 26, 2018, which claims priority under 35 U.S.C. § 119(a) to Japanese Patent Application No. 2017-067548 filed on Mar. 30, 2017. The above application is hereby expressly incorporated by reference, in its entirety, into the present application.

BACKGROUND OF THE INVENTION

1. Field of the Invention

The present invention relates to an ultrasound diagnostic apparatus and a method for controlling the ultrasound diagnostic apparatus, and more particularly, to an ultrasound diagnostic apparatus that estimates blood flow information from a Doppler signal and a method for controlling the ultrasound diagnostic apparatus.

2. Description of the Related Art

In the related art, an ultrasound diagnostic apparatus has been used in order to obtain blood flow information in a subject. In general, the ultrasound diagnostic apparatus comprises a transducer array in which a plurality of elements are arranged. In a state in which the ultrasound probe comes into contact with the body surface of the subject, ultrasound beams are transmitted from the transducer array to the subject and the transducer array receives ultrasound echoes from the subject to acquire a Doppler signal. In addition, the ultrasound diagnostic apparatus generates a Doppler image which is blood flow information on the basis of frequency shift information included in the obtained Doppler signal.

An example of the Doppler image obtained by the ultrasound diagnostic apparatus is a color Doppler image obtained by imparting colors to the image of blood according to, for example, the flow direction of blood and the flow rate of blood. The color Doppler image is an image generated by a color flow mapping method. The color flow mapping method performs a filtering process using a so-called moving target indicator (MTI) filter for a data string on the same scanning line and at the same position such that clutter, which is a signal obtained from a slow-moving tissue, is suppressed, thereby extracting a blood flow signal component. The clutter component of the Doppler signal needs to be suppressed in order to obtain a color Doppler image with high accuracy.

Various ultrasound diagnostic apparatuses which can suppress the clutter component of the Doppler signal with high accuracy have been proposed. For example, an ultrasound diagnostic apparatus disclosed in JP2014-158698A calculates a correlation matrix in a scanning range from a data string of reflected wave data at the same position on the same scanning line, calculates a filter coefficient of an MTI filter from the result of principal component analysis based on the correlation matrix, extracts an ultrasound beam reflected from a moving body using the MTI filter to estimate the information of the moving body, and generates an ultrasound image on the information of the moving body. In addition, the ultrasound diagnostic apparatus disclosed in JP2014-158698A uses the average value of the correlation matrix in the scanning range as the correlation matrix used for the principal component analysis.

Further, for example, an ultrasound diagnostic apparatus disclosed in JP2004-073672A performs an autocorrelation operation for a received Doppler signal to estimate the center frequency and variance of a clutter component and shifts the frequency of the clutter component to the vicinity of zero. Furthermore, the ultrasound diagnostic apparatus disclosed in JP2004-073672A applies an MTI filter to the clutter component whose frequency has been shifted.

SUMMARY OF THE INVENTION

However, the movement of the body of a subject is likely to occur due to, for example, the pulsation of the heart and large blood vessels and the breathing of the subject. In addition, the relative movement of the body of the subject associated with the movement of an ultrasound probe is likely to occur. In this case, since the movement of the tissue of the subject which is the source of the clutter component increases, the spatial correlation of the clutter component is reduced. In the technique disclosed in JP2014-158698A, it is difficult to estimate the clutter component with high accuracy.

In addition, in the technique disclosed in JP2004-073672A, in a case in which the movement speed of the tissue of the subject which is the source of the clutter component is sufficiently high and in a case in which the movement speed of the tissue of the subject which is the source of the clutter component changes greatly, only the phase correction based on the center frequency of the clutter component is insufficient to obtain the effect of suppressing the clutter component.

Further, in the techniques disclosed in JP2014-158698A and JP2004-073672A, in a case in which the movement of the tissue of the subject which is the source of the clutter component is large, Doppler analysis is collectively performed for the reflected waves of ultrasonic beams transmitted to blood flowing in the blood vessels and the reflected waves of ultrasonic beams transmitted to the tissue that has moved largely. As a result, so-called motion artifacts occur and it is difficult to obtain blood flow information with high accuracy.

The invention has been made in view of the above-mentioned problems and an object of the invention is to provide an ultrasound diagnostic apparatus that can obtain blood flow information with high accuracy, without generating motion artifacts as much as possible, even in a case the tissue of a subject moves largely and a method for controlling the ultrasound diagnostic apparatus.

In order to achieve the object, according to the invention, there is provided an ultrasound diagnostic apparatus comprising: a data acquisition unit that repeatedly transmits an ultrasound beam to a subject a plurality of times in a range over a plurality of scanning lines to acquire a time-series data string of reflected waves from the subject; a positional deviation amount estimation unit that estimates an amount of relative positional deviation of a scatterer of the subject which is included in the time-series data string; a data exclusion unit that excludes time-series data satisfying an exclusion condition based on the amount of positional deviation of the scatterer estimated by the positional deviation amount estimation unit from the time-series data string to select analysis target data; an MTI filter unit that removes a clutter component from the analysis target data selected by the data exclusion unit; and a blood flow information estimation unit that analyzes the analysis target data from which the clutter component has been removed by the MTI filter unit to estimate blood flow information of the subject.

The positional deviation amount estimation unit may estimate a relative movement distance of the scatterer on the basis of the time-series data string. The data exclusion unit may exclude, from the time-series data string, a plurality of time-series data items in which the movement distance of the scatterer estimated by the positional deviation amount estimation unit is greater than a predetermined threshold value.

Alternatively, the positional deviation amount estimation unit may set a plurality of extracted data items which have been extracted at an interval of a predetermined number of data items in the time-series data string and estimate the relative movement distance of the scatterer for the plurality of extracted data items. The data exclusion unit may exclude, from the time-series data string, a plurality of time-series data items in a range of the plurality of extracted data items in which the movement distance of the scatterer estimated by the positional deviation amount estimation unit is greater than a predetermined threshold value.

The MTI filter unit may change filter characteristics for the analysis target data in which the movement distance of the scatterer has been estimated by the positional deviation amount estimation unit such that, as the movement distance of the scatterer becomes longer, an amount of attenuation of a low-frequency component becomes larger.

Alternatively, the MTI filter unit may calculate an average value of a correlation matrix of the analysis target data in a predetermined range in the range over the plurality of scanning lines and perform principal component analysis having clutter as a main component, using the average value of the correlation matrix, to remove the clutter component from the analysis target data.

The positional deviation amount estimation unit may estimate a motion vector which has a relative movement distance and a movement direction of the scatterer included in the time-series data as an absolute value and a direction, respectively. The data exclusion unit may sequentially connect starting points and end points of a plurality of the motion vectors estimated from the time-series data string in time series, arrange data points corresponding to a plurality of time-series data items included in the time-series data string on a data plane, sequentially extract a section of a plurality of the data points, which are continuous in time series and are included in any one of a plurality of circles that have the plurality of data points as centers and have the same radius, as the analysis target data in descending order of the number of data points, and exclude time-series data corresponding to the data point included in only one circle.

Alternatively, the positional deviation amount estimation unit may set a plurality of extracted data items which have been extracted at an interval of a predetermined number of data items in the time-series data string and estimate a motion vector which has a relative movement distance and a movement direction of the scatterer as an absolute value and a direction, respectively, for each of the plurality of extracted data items. The data exclusion unit may sequentially connect starting points and end points of a plurality of the motion vectors estimated from the plurality of extracted data items in time series, arrange data points corresponding to the extracted data items on a data plane, sequentially extract a section of a plurality of the data points, which are continuous in time series and are included in any one of a plurality of circles that have the plurality of data points as centers and have the same radius, as the analysis target data in descending order of the number of data points, and exclude time-series data corresponding to the data point included in only one circle.

The MTI filter unit may change filter characteristics for a plurality of the analysis target data items corresponding to each extracted section of the plurality of data points such that, as a total sum of lengths of the motion vectors included in the section becomes larger, an amount of attenuation of a low-frequency component becomes larger.

Alternatively, the positional deviation amount estimation unit may estimate a plurality of neighboring displacement vectors which have relative movement distances and movement directions of points included in the time-series data string in the range over the plurality of scanning lines as absolute values and directions, respectively. The MTI filter unit may give a larger weight to a plurality of the analysis target data items as a correlation between the motion vector and each of the neighboring displacement vectors becomes higher, calculate an average value of a correlation matrix for a plurality of the analysis target data items in a predetermined range in the range over the plurality of scanning lines, and perform principal component analysis having clutter as a main component, using the average value of the correlation matrix, to remove the clutter component from the remaining analysis target data items.

Preferably, the ultrasound diagnostic apparatus further comprises: a correlation coefficient calculation unit that calculates a correlation coefficient in the same region of interest in the time-series data string; and a data division unit that divides the time-series data string into a first data group including time-series data items whose correlation coefficient calculated by the correlation coefficient calculation unit is greater than a predetermined value, and a second data group including time-series data items whose correlation coefficient is equal to or less than the predetermined value.

The MTI filter unit may set filter characteristics such that filter characteristics for the time-series data items in the first data group are different from filter characteristics for the time-series data items in the second data group.

The data division unit may calculate an amount of change in a brightness value in the same region of interest included in time-series data items which are adjacent to each other in the second data group and divide the time-series data items in the second data group into a third data group in which the amount of change in the brightness value is greater than a predetermined value and a fourth data group in which the amount of change in the brightness value is equal to or less than the predetermined value.

The MTI filter unit may set filter characteristics such that filter characteristics for the time-series data items in the third data group are different from filter characteristics for the time-series data items in the fourth data group.

Alternatively, the data exclusion unit may exclude the time-series data items in the fourth data group.

The MTI filter unit may give a larger weight to the analysis target data as the correlation coefficient calculated for a plurality of points in the range over the plurality of scanning lines becomes larger, calculate an average value of a correlation matrix in a predetermined range in the range over the plurality of scanning lines, and perform principal component analysis having clutter as a main component, using the average value of the correlation matrix, to remove the clutter component from the analysis target data.

The data exclusion unit may exclude time-series data items which are continuous in time series and whose number is less than a predetermined number of data items among the time-series data items divided by the data division unit.

The data exclusion unit may exclude time-series data items which are continuous in time series and whose number is less than a predetermined number of data items among a plurality of time-series data items which remain as a result of the exclusion of the time-series data items.

Preferably, the MTI filter unit removes the clutter component from the analysis target data in each division section including a plurality of the analysis target data items divided from the time-series data string. Preferably, the blood flow information estimation unit estimates the blood flow information from the plurality of analysis target data items from which the clutter component has been removed by the MTI filter unit in each division section. Preferably, the ultrasound diagnostic apparatus further comprises a blood flow information combination unit that combines the blood flow information estimated by the blood flow information estimation unit in a plurality of the division sections.

According to the invention, there is provided a method for controlling an ultrasound diagnostic apparatus. The method comprises: repeatedly transmitting an ultrasound beam to a subject a plurality of times in a range over a plurality of scanning lines to acquire a time-series data string of reflected waves from the subject; estimating an amount of relative positional deviation of a scatterer of the subject which is included in the time-series data string; excluding time-series data satisfying an exclusion condition based on the estimated amount of positional deviation from the time-series data string to select analysis target data; removing a clutter component from the selected analysis target data; and analyzing the analysis target data from which the clutter component has been removed to estimate blood flow information of the subject.

According to the invention, the ultrasound diagnostic apparatus estimates the amount of relative positional deviation of the scatterer included in the time-series data string and excludes time-series data satisfying the exclusion condition from the time-series data string on the basis of the amount of positional deviation. Therefore, even in a case in which the tissue of the subject moves largely, it is possible to obtain blood flow information with high accuracy.

DESCRIPTION OF THE PREFERRED EMBODIMENTS

Hereinafter, embodiments of the invention will be described with reference to the accompanying drawings.

Embodiment 1

Figure 1:
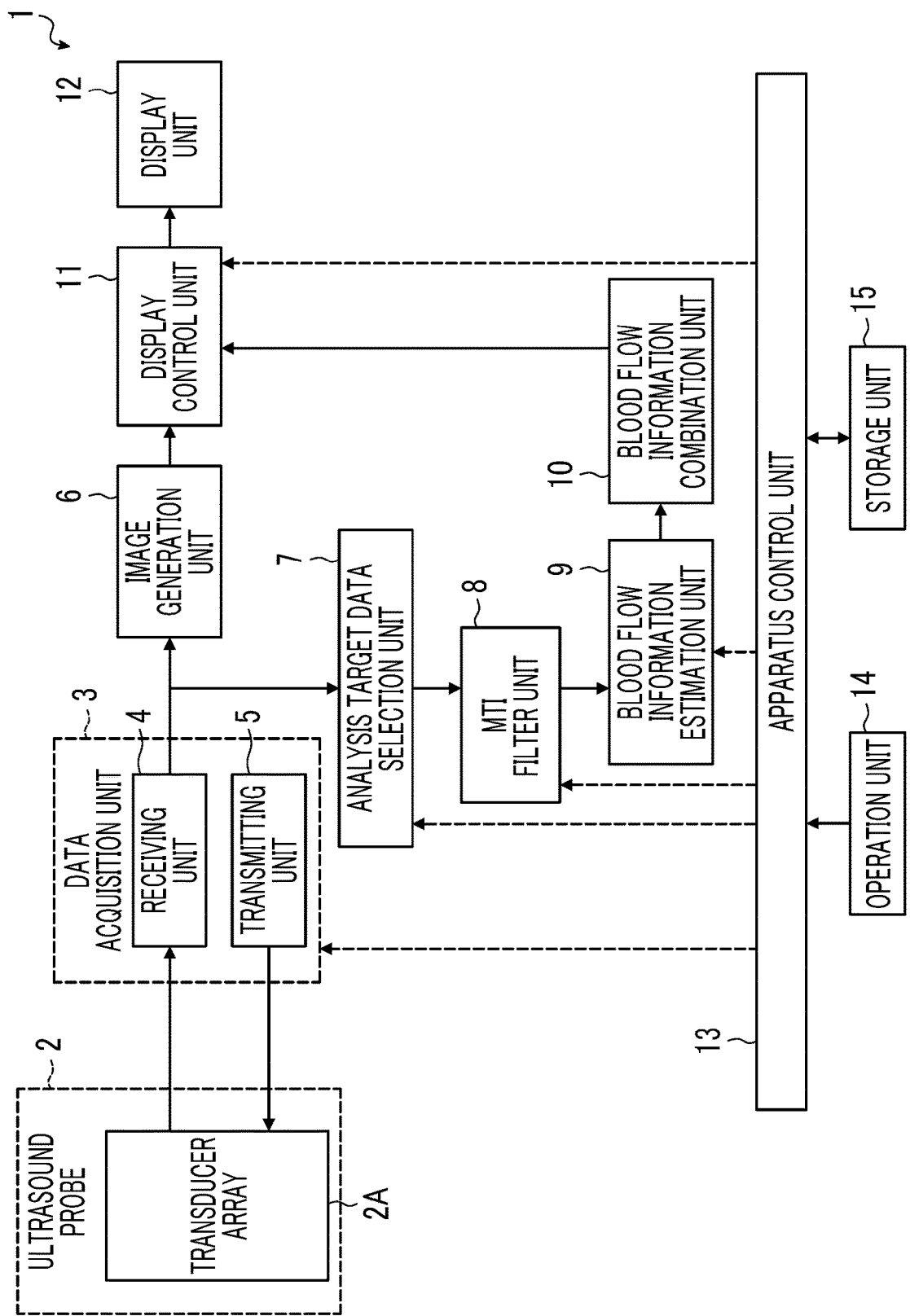
FIG. 1 is a block diagram illustrating the configuration of an ultrasound diagnostic apparatus according to Embodiment 1 of the invention.

FIG. 1 illustrates the configuration of an ultrasound diagnostic apparatus according to Embodiment 1 of the invention. An ultrasound diagnostic apparatus 1 comprises an ultrasound probe 2 having a transducer array 2A provided therein and a data acquisition unit 3 is connected to the ultrasound probe 2.

The data acquisition unit 3 includes a receiving unit 4 and a transmitting unit 5 which are connected to the transducer array 2A of the ultrasound probe 2 and an image generation unit 6 is connected to the receiving unit 4. In addition, an analysis target data selection unit 7 is connected to the receiving unit 4 and an MTI filter unit 8 is connected to the analysis target data selection unit 7. A blood flow information estimation unit 9 is connected to the MTI filter unit 8 and a blood flow information combination unit 10 is connected to the blood flow information estimation unit 9. Further, a display control unit 11 is connected to the image generation unit 6 and the blood flow information combination unit 10 and a display unit 12 is connected to the display control unit 11.

Furthermore, an apparatus control unit 13 is connected to the data acquisition unit 3, the analysis target data selection unit 7, the MTI filter unit 8, the blood flow information estimation unit 9, and the display control unit 11 and an operation unit 14 and a storage unit 15 are connected to the apparatus control unit 13. The apparatus control unit 13 and the storage unit 15 are connected to each other such that they can transmit and receive information in both directions.

The transducer array 2A of the ultrasound probe 2 illustrated in FIG. 1 includes a plurality of elements (ultrasound transducers) that are one-dimensionally or two-dimensionally arranged.

Each of the elements transmits ultrasonic waves in response to a driving signal supplied from the transmitting unit 5. In addition, each of the elements receives reflected waves from a subject and outputs a received signal. Each element is, for example, a transducer in which electrodes are formed at both ends of a piezoelectric body made of piezoelectric ceramic typified by lead zirconate titanate (PZT), a polymer piezoelectric element typified by polyvinylidene difluoride (PVDF), or a piezoelectric single crystal typified by lead magnesium niobate-lead titanate (PMN-PT).

In a case in which a pulsed voltage or a continuous-wave voltage is applied to the electrodes of the transducer, the piezoelectric body is expanded and contracted and pulsed or continuous ultrasonic waves are generated from each transducer. An ultrasound beam is formed from a composite wave of the ultrasonic waves. In addition, each transducer receives propagated ultrasonic waves, is expanded and contracted, and generates an electric signal. The electric signal is output as a received ultrasound signal. The electric signal is output as a received ultrasound signal from each transducer to the receiving unit 4.

Figure 2:
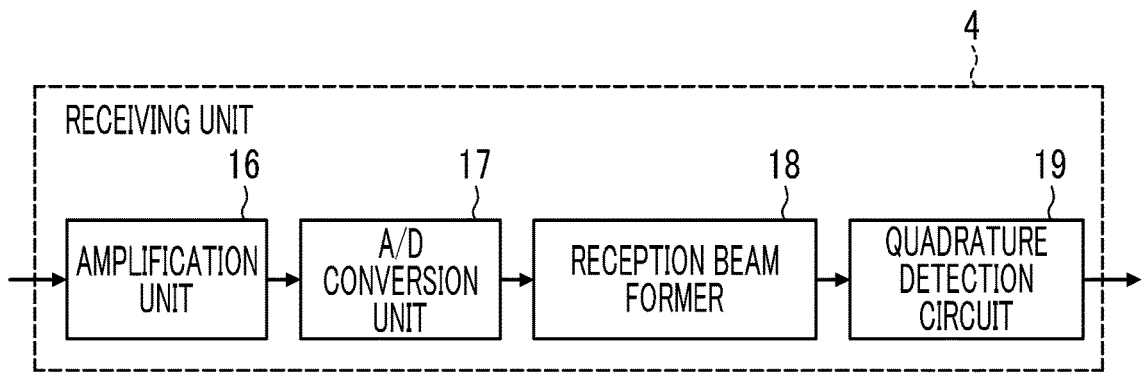
FIG. 2 is a block diagram illustrating the internal configuration of a receiving unit in Embodiment 1 of the invention.

As illustrated in FIG. 2, the receiving unit 4 of the data acquisition unit 3 has a configuration in which an amplification unit 16, an analog/digital (A/D) conversion unit 17, a reception beam former 18, and a quadrature detection circuit 19 are connected in series to each other. In the receiving unit 4, the amplification unit 16 amplifies the received signal output from each element of the transducer array 2A. The A/D conversion unit 17 converts the amplified received signal into a digital signal to generate digital element data and outputs the digital element data to the reception beam former 18.

The reception beam former 18 performs a reception focusing process that applies a delay to each received data item according to a sound speed set on the basis of a reception delay pattern selected according to a control signal from the apparatus control unit 13 and adds (phasing addition) the data items. A sound ray signal in which the focus of an ultrasound echo is narrowed is generated by the reception focusing process. The generated sound ray signal is output to the quadrature detection circuit 19.

The quadrature detection circuit 19 converts the sound ray signal generated by the reception beam former 18 into a complex signal and outputs the complex signal to the image generation unit 6 and the analysis target data selection unit 7.

The transmitting unit 5 of the data acquisition unit 3 includes, for example, a plurality of pulse generators, adjusts the amount of delay of each driving signal such that the ultrasound waves transmitted from the plurality of elements of the transducer array 2A form an ultrasound beam on the basis of the transmission delay pattern selected according to the control signal from the apparatus control unit 13, and supplies each driving signal to the plurality of elements.

In a case in which a brightness-mode (B-mode) image which is image information related to the shape of the tissues of the subject is generated on the basis of the intensity of reflected waves from a scatterer in the subject, the data acquisition unit 3 transmits ultrasound beams while sequentially moving the transmission position of the ultrasound beams and receives reflected waves at a plurality of positions.

In addition, in a case in which a Doppler image, such as a color Doppler image or a power Doppler image, is generated on the basis of frequency shift information included in the reflected waves from the scatterer in the subject, the data acquisition unit 3 repeatedly transmits ultrasound beams to the same scanning line a plurality of times in a range over a plurality of scanning lines and receives a plurality of reflected waves from the same position.

Figure 3:
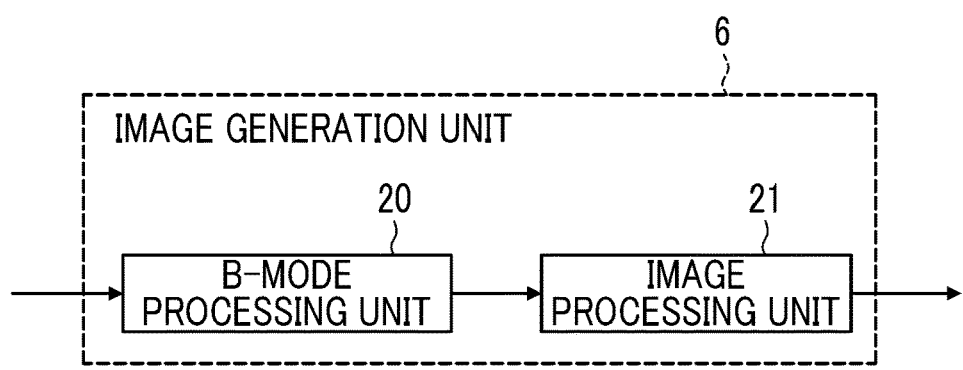
FIG. 3 is a block diagram illustrating the internal configuration of an image generation unit in Embodiment 1 of the invention.

As illustrated in FIG. 3, the image generation unit 6 has a configuration in which a B-mode processing unit 20 and an image processing unit 21 are sequentially connected in series to each other.

The B-mode processing unit 20 corrects the attenuation of the signal generated by the receiving unit 4 which is caused by a propagation distance according to the depth of the position where the ultrasound waves are reflected and then performs an envelope detection process to generate a B-mode image signal which is tomographic image information related to the tissues in the subject. The B-mode image signal generated by the B-mode processing unit 20 is output to the image processing unit 21.

The image processing unit 21 converts the B-mode image signal generated by the B-mode processing unit 20 into an image signal based on a general television signal scanning system (raster conversion, performs various types of necessary image processing including a gradation process for the B-mode image signal, and outputs the B-mode image signal to the display control unit 11.

Figure 4:
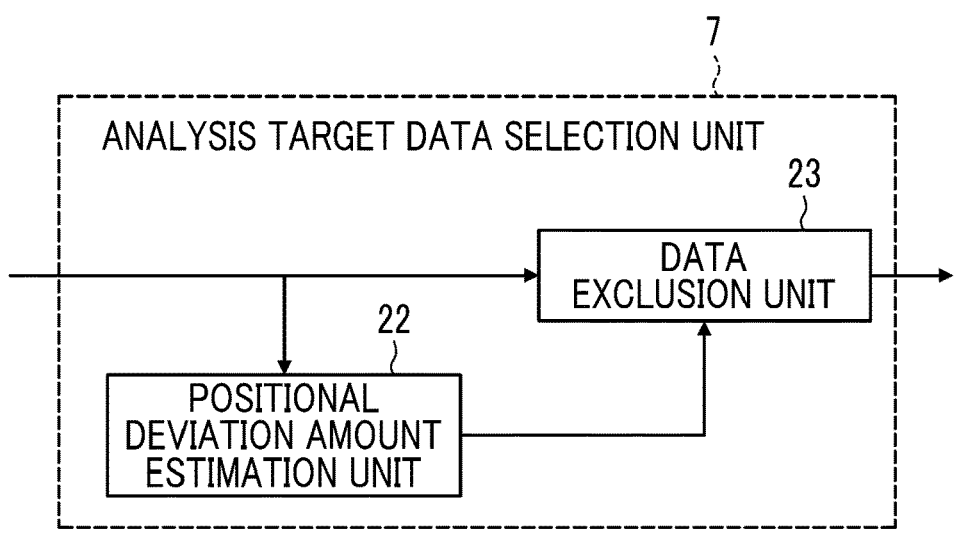
FIG. 4 is a block diagram illustrating the internal configuration of an analysis target data selection unit in Embodiment 1 of the invention.

As illustrated in FIG. 4, the analysis target data selection unit 7 includes a positional deviation amount estimation unit 22 and a data exclusion unit 23. The data received by the analysis target data selection unit 7 from the receiving unit 4 is a data string which is acquired in order to generate a Doppler image and a time-series data string which is obtained by performing the transmission of ultrasound beams to the subject for the same scanning line in a range over a plurality of scanning lines a plurality of times and receiving a plurality of reflected waves from the same position.

The positional deviation amount estimation unit 22 estimates the amount of positional deviation of a scatterer of the subject which is included in the time-series data string received from the receiving unit 4. For example, the positional deviation amount estimation unit 22 performs a process, such as template matching, for the regions of interest, which have, as the center, the same scatterer included in two time-series data items acquired at different points of time by the data acquisition unit 3, to estimate the amount of relative positional deviation of the scatterer. Information related to the amount of positional deviation of the scatterer estimated by the positional deviation amount estimation unit 22 is transmitted to the data exclusion unit 23.

The data exclusion unit 23 receives the information related to the amount of positional deviation of the scatterer included in the time-series data string from the positional deviation amount estimation unit 22 and receives the time-series data string from the receiving unit 4 of the data acquisition unit 3. The data exclusion unit 23 extracts time-series data satisfying exclusion conditions based on the amount of positional deviation of the scatterer from the time-series data string and selects analysis target data to be subjected to Doppler analysis. In addition, as a result of the exclusion of the time-series data by the data exclusion unit 23, in some cases, analysis target data items which are continuous in time series are divided into a plurality of division sections. In this case, each of the plurality of division sections of the analysis target data items is transmitted to the MTI filter unit 8.

The MTI filter unit 8 has predetermined filtering characteristics and performs a filtering process for removing a clutter component from the analysis target data selected by the data exclusion unit 23 of the analysis target data selection unit 7, using the predetermined filtering characteristics.

As such, the removal of the clutter component from the analysis target data by the MTI filter unit 8 makes it possible to reduce the influence of extra frequency components other than a blood flow in a case in which Doppler analysis is performed. Therefore, it is possible to improve the accuracy of blood flow information obtained as a result of the Doppler analysis.

The blood flow information estimation unit 9 performs Doppler analysis for the analysis target data, from which the clutter component has been removed by the MTI filter unit 8, to estimate the blood flow information of the subject. Various methods can be used as a method that performs the Doppler analysis for the analysis target data to estimate the blood flow information. For example, the blood flow information estimation unit 9 can estimate the blood flow information using a so-called autocorrelation method.

The blood flow information combination unit 10 combines a plurality of blood flow information items estimated from the analysis target data items in each division section by the blood flow information estimation unit 9 in a case in which the analysis target data items are divided into a plurality of division sections by the data exclusion unit 23 of the analysis target data selection unit 7.

As illustrated in FIG. 1, the display control unit 11 of the ultrasound diagnostic apparatus 1 displays an ultrasound image on the display unit 12 on the basis of the B-mode image signal generated by the image generation unit 6 and the blood flow information of the subject generated by the blood flow information estimation unit 9 and the blood flow information combination unit 10. Here, the ultrasound image is obtained by superimposing a Doppler image, such as a color Doppler image or a power Doppler image, on the B-mode image.

The display unit 12 includes a display device, such as a liquid crystal display (LCD), and displays the ultrasound image under the control of the apparatus control unit 13.

The apparatus control unit 13 controls each unit of the ultrasound diagnostic apparatus 1 on the basis of a command input by an operator through the operation unit 14.

The operation unit 14 is used by the operator to perform an input operation and may comprise, for example, a keyboard, a mouse, a trackball, and a touch panel.

The storage unit 15 stores, for example, an operation program of the ultrasound diagnostic apparatus 1, and may be a recording medium, such as a hard disk drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), or a universal serial bus memory (USB memory), or a server.

The image generation unit 6, the analysis target data selection unit 7, the MTI filter unit 8, the blood flow information estimation unit 9, the blood flow information combination unit 10, the display control unit 11, and the apparatus control unit 13 are configured by a central processing unit (CPU) and a control program that causes the CPU to perform various processes. However, these units may be configured by a digital circuit and a computer. In addition, some or all of the image generation unit 6, the analysis target data selection unit 7, the MTI filter unit 8, the blood flow information estimation unit 9, the blood flow information combination unit 10, the display control unit 11, and the apparatus control unit 13 may be integrated into one CPU.

Next, a blood flow information acquisition operation of the ultrasound diagnostic apparatus 1 according to Embodiment 1 will be described with reference to a flowchart illustrated in FIG. 5.

First, in Step S1, the positional deviation amount estimation unit 22 of the analysis target data selection unit 7 sets a plurality of extracted data items which are data items discretely extracted at an interval of a predetermined number of data items from the acquired time-series data string.

The interval between the extracted data items can be set to the number of data items where the accuracy of Doppler analysis is not reduced. For example, the interval can be set to four or more data items. The setting of a plurality of extracted data items from the time-series data string makes it possible to reduce the computation load required for calculating the amount of positional deviation. In addition, sine the amount of positional deviation of the scatterer included in the time-series data string is estimated for the discretely extracted data items, it is possible to prevent the estimation of the amount of positional deviation of the scatterer at a very short time interval and thus to estimate the amount of positional deviation of the scatterer with sufficiently high accuracy.

Then, in Step S2, the positional deviation amount estimation unit 22 of the analysis target data selection unit 7 estimates the amount of relative positional deviation of the scatterer included in extracted data items which are adjacent to each other in time series among the plurality of extracted data items. Here, a case in which the amount of relative positional deviation of the scatterer estimated by the positional deviation amount estimation unit 22 is the amount of relative movement of the scatterer will be described.

Figure 6:
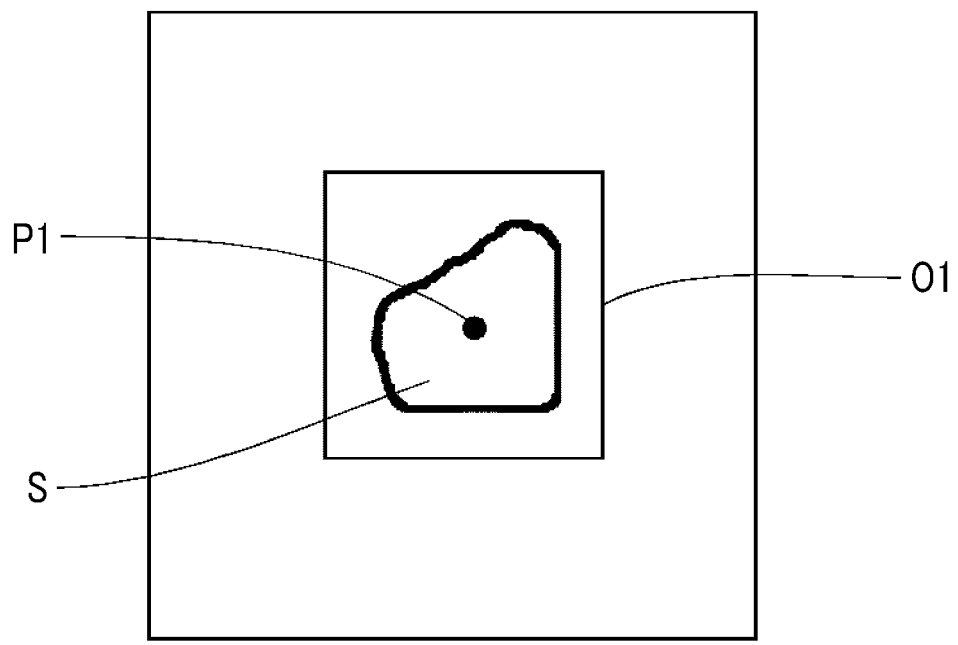
FIG. 6 is a conceptual diagram illustrating a scatterer included in extracted data which is set by a positional deviation amount estimation unit in Embodiment 1 of the invention.
Figure 7:
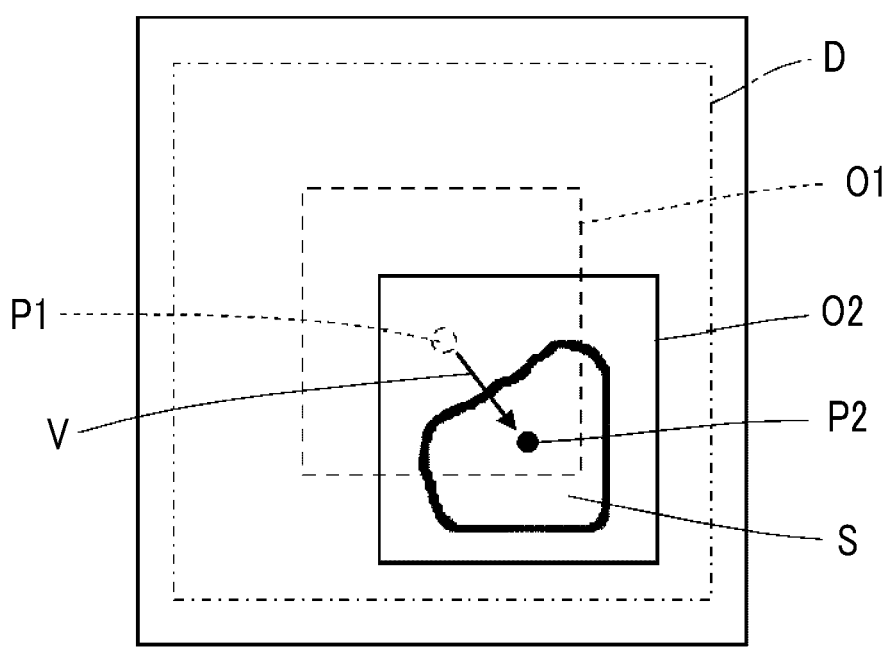
FIG. 7 is a conceptual diagram illustrating the scatterer which has been shifted and is included in the extracted data set by the positional deviation amount estimation unit in Embodiment 1 of the invention.

In this case, first, the positional deviation amount estimation unit 22 sets one of the extracted data items which are adjacent to each other in time series as reference data in template matching. In the reference extracted data, the positional deviation amount estimation unit 22 sets a region of interest O1 such that a point P1 is disposed in a scatterer S included in the extracted data as illustrated in FIG. 6. The region of interest O1 is set such that the point P1 is located at the center. Then, in the other extracted data, the positional deviation amount estimation unit 22 sets a search region D which is larger than the region of interest O1 and has the point P1 disposed in the region of interest O1 as the center as illustrated in FIG. 7. The positional deviation amount estimation unit 22 calculates the similarity between the region of interest O1 in the one extracted data item which is the reference extracted data and the region of interest O1 in the other extracted data item while moving the region of interest O1 in the search region D and specifies a region of interest O2 with the highest similarity. In addition, the positional deviation amount estimation unit 22 estimates a motion vector V from the point P1 of the region of interest O1 in the reference extracted data to a point P2 of the region of interest O2 in the other extracted data item, calculates the absolute value of the motion vector V, and estimates a relative movement distance of the scatterer S.

Figure 8:
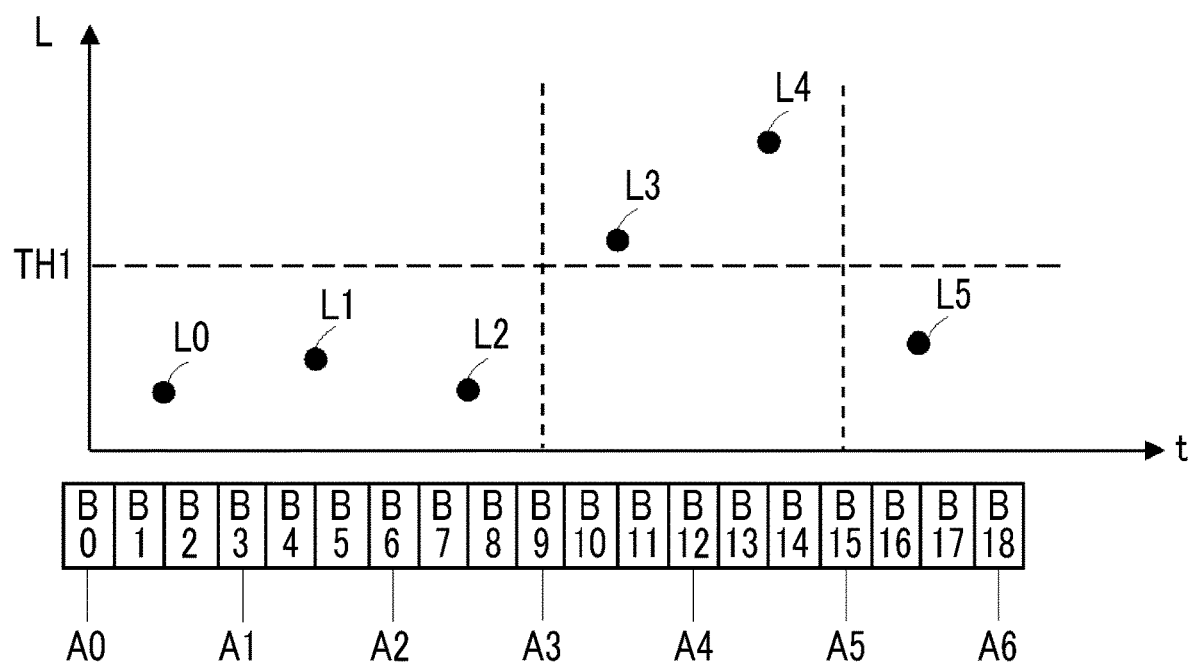
FIG. 8 is a diagram illustrating the amount of movement of the scatterer included in each extracted data item together with a plurality of extracted data items and a time-series data string.

In a case in which the relative movement distance of the scatterer is estimated from each of the plurality of extracted data items which are adjacent to each other in time series, in Step S3, the data exclusion unit 23 of the analysis target data selection unit 7 compares the values of a plurality of movement distances of the scatterer estimated in Step S2 with a predetermined threshold value. Then, the data exclusion unit 23 excludes, from the time-series data string, a plurality of time-series data items in the range of the extracted data items in which the movement distance of the scatterer is greater than the threshold value and selects the remaining time-series data items as the analysis target data to be subjected to Doppler analysis. Here, FIG. 8 illustrates an example in which a plurality of movement distances of the scatterer are arranged together with the time-series data string and a plurality of extracted data items. In the example illustrated in FIG. 8, L indicates the relative movement distance of the scatterer, t indicates time, and TH1 indicates a threshold value determined with respect to the movement distance L. In addition, B0 to B18 indicate time-series data items forming a time-series data string and A0 to A6 indicate extracted data items. Further, L0 to L5 indicate the movement distances of the scatterer estimated from the extracted data items which are adjacent to each other in time series among the extracted data items A0 to A6.

In the example illustrated in FIG. 8, both the movement distance L3 of the scatterer estimated from the extracted data items A3 and A4 and the movement distance L4 of the scatterer estimated from the extracted data items A4 and A5 are greater than the threshold value TH1. In this case, the data exclusion unit 23 excludes the time-series data items B9 to B15 in the range of the adjacent extracted data items A3 and A4 and the adjacent extracted data items A4 and A5 from the time-series data string and the remaining time-series data items B0 to B8 and B16 to B18 as the analysis target data items to be subjected to Doppler analysis. Further, in the example illustrated in FIG. 8, the analysis target data items are divided into a division section including the time-series data items B0 to B8 which are continuous in time series and a division section including the time-series data items B16 to B18 which are continuous in time series.

As such, since the time-series data in which the movement distance of the scatterer is greater than the threshold value is excluded, it is possible to prevent both the tissue movement and the blood flow motion of the subject during the Doppler analysis and thus to improve the accuracy of estimating blood flow information.

Figure 9:
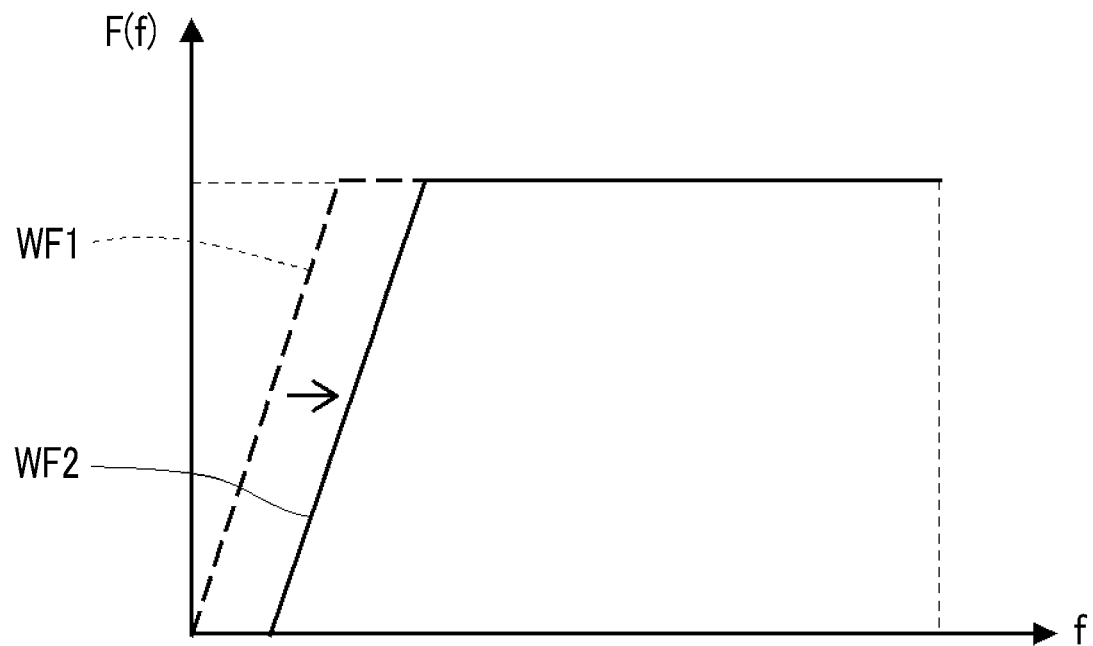
FIG. 9 is a diagram illustrating a change in the characteristics of an MTI filter.
Figure 10:
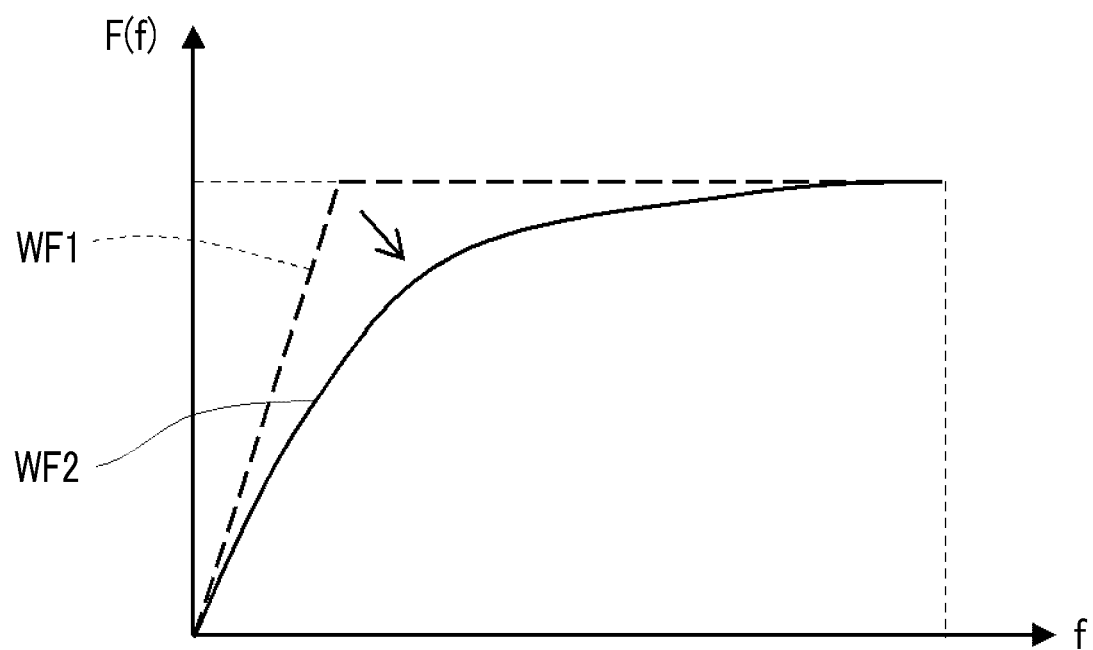
FIG. 10 is a diagram illustrating another example of the change in the characteristics of the MTI filter.

Then, in Step S4, the MTI filter unit 8 performs a filtering process for the analysis target data selected in Step S3 such that a clutter component is removed. In this case, the MTI filter unit 8 can change predetermined filter characteristics according to the estimated movement distance of the scatterer. For example, the MTI filter unit 8 can change a predetermined filter waveform WF1 such that the attenuation of a low-frequency component of the analysis target data becomes larger as the estimated movement distance of the scatterer becomes large to obtain a filter waveform WF2 as illustrated in FIG. 9. In addition, the MTI filter unit 8 may change the predetermined filter waveform WF1 to a curve-shaped filter waveform WF3 in order to increase the attenuation of a low-frequency component of the analysis target data as the estimated movement distance of the scatterer increases as illustrated in FIG. 10. Here, F(f) in FIG. 9 and FIG. 10 indicates filter characteristics applied to the analysis target data and f indicates the frequency of the analysis target data. The MTI filter unit 8 removes a clutter component from the analysis target data by attenuating the low-frequency component of the analysis target data using the filter characteristics.

The blood flow information estimation unit 9 performs Doppler analysis for a plurality of analysis target data items, from which the clutter components have been removed in Step S4, to estimate the blood flow information of the subject in Step S5. The blood flow information estimation unit 9 can use various methods as a method for performing Doppler analysis for a plurality of analysis target data items. For example, the blood flow information estimation unit 9 performs an autocorrelation operation for a plurality of analysis target data items to estimate blood flow information, such as the center frequency and power of a blood flow. In a case in which the analysis target data items are divided into a plurality of division sections in Step S3, the blood flow information of each division section of the analysis target data items is estimated.

As such, in a case in which the analysis target data items are divided into a plurality of division sections in Step S3, in Step S6, the blood flow information combination unit 10 combines the blood flow information items estimated for the plurality of division sections. Then, the blood flow information acquisition operation ends.

In the above-mentioned ultrasound diagnostic apparatus 1 according to Embodiment 1, the time-series data in which the movement distance of the scatterer is equal to or less than a predetermined threshold value and which is included in the time-series data string is selected as the analysis target data to be subjected to Doppler analysis. Further, the ultrasound diagnostic apparatus 1 removes a clutter component from the analysis target data and estimates the blood flow information of the subject from the analysis target data from which the clutter component has been removed. Therefore, even in a case in which the tissue of the subject moves largely, the ultrasound diagnostic apparatus 1 can remove a component caused by the large movement of the tissue of the subject from the analysis target data to be subjected to Doppler analysis and can obtain blood flow information with high accuracy.

Figure 5:
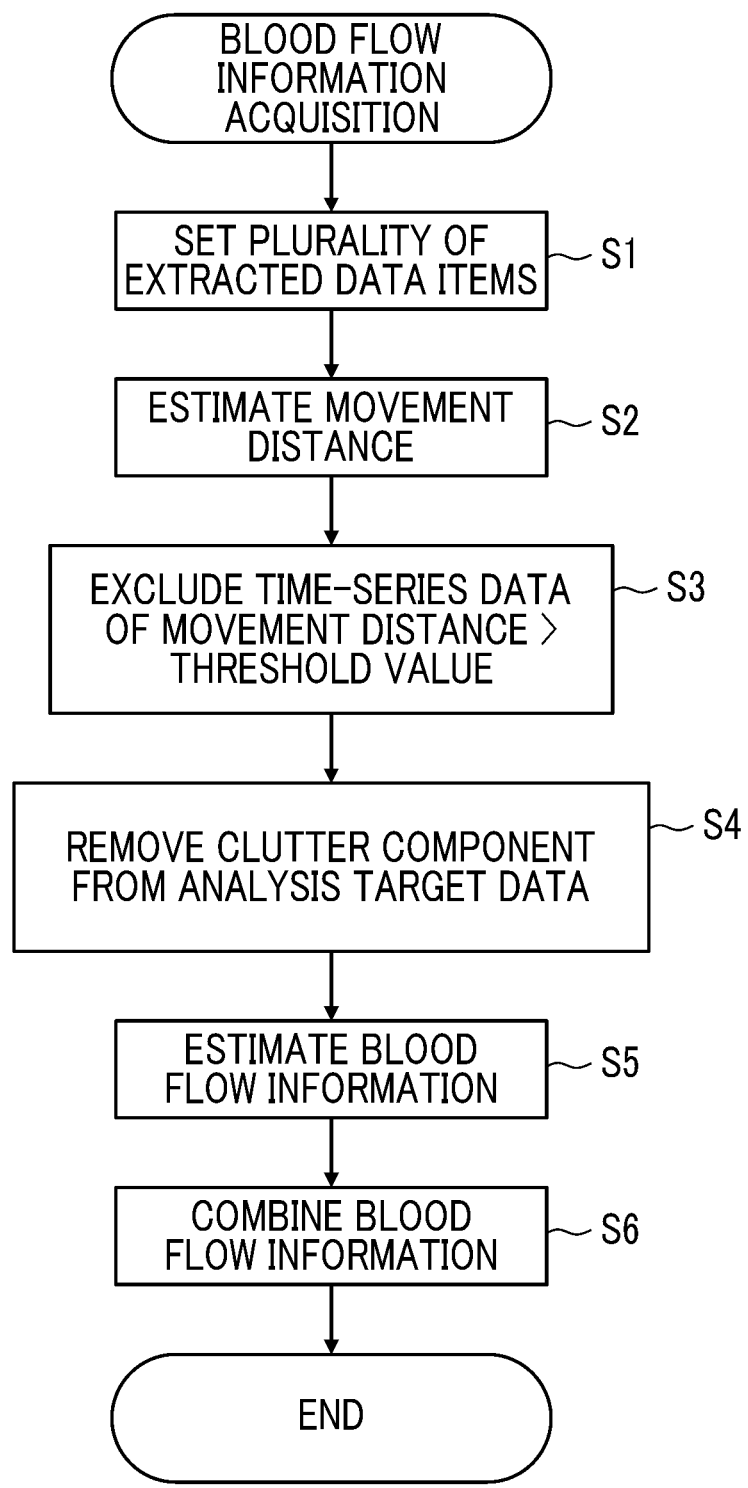
FIG. 5 is a flowchart illustrating a blood flow information acquisition operation of the ultrasound diagnostic apparatus according to Embodiment 1 of the invention.

The example in which the positional deviation amount estimation unit 22 of the analysis target data selection unit 7 estimates the motion vector of the scatterer included in the time-series data string using a plurality of extracted data items in Step S2 of the flowchart illustrated in FIG. 5 has been described. However, the positional deviation amount estimation unit 22 may estimate the motion vector of the scatterer from a plurality of adjacent time-series data items forming the time-series data string as long as it can estimate the motion vector of the scatterer with high accuracy. For example, in a case in which the time interval between a plurality of time-series data items forming the time-series data string is sufficiently long, the positional deviation amount estimation unit 22 can estimate the motion vector of the scatterer from that time-series data items that are adjacent to each other in time series.

Further, the positional deviation amount estimation unit 22 estimates a motion vector in the data items of interest which are adjacent to each other in time series, using template matching. However, in a case in which template matching is performed for all of the data items in the search region D, a lot of time may be required due to the calculation performance of the ultrasound diagnostic apparatus 1. In this case, the positional deviation amount estimation unit 22 can perform template matching using extracted data obtained by thinning out data in the search region D in order to reduce the amount of calculation required for the template matching. Further, the positional deviation amount estimation unit 22 may perform data interpolation for the thinned-out data.

In a case in which the time-series data string is divided into a plurality of division sections, the data exclusion unit 23 of the analysis target data selection unit 7 may exclude the time-series data items which are continuous in time series and whose number is less than a predetermined number of data items. During Doppler analysis, as the number of analysis target data items which are continuous in time series becomes larger, it is possible to estimate blood flow information with higher accuracy. Therefore, the configuration in which the data exclusion unit 23 excludes the time-series data items which are continuous in time series and whose number is less than a predetermined value makes it possible to improve the accuracy of estimating blood flow information.

It is desirable that the threshold value compared with the value of the movement distance of the scatterer by the data exclusion unit 23 is set according to the performance of the filter in the MTI filter unit 8. In the MTI filter according to the related art, in a case in which the movement distance of the scatterer is larger than a wavelength corresponding to the center frequency of an ultrasonic beam, a clutter component is unlikely to be sufficiently suppressed. Therefore, for example, in a case in which an MTI filter having the same performance as the MTI filter according to the related art is used, it is desirable that the threshold value of the movement distance of the scatterer is set to one-half to one times the wavelength corresponding to the center frequency of the ultrasound beam.

In a case in which the blood flow information is combined in Step S6, the blood flow information combination unit 10 can perform weighted addition for the blood flow information according to the number of analysis target data items included in each of the plurality of division sections. This is because the accuracy of estimating the blood flow information depends on the number of analysis target data items that are continuous in time series. Therefore, for example, the blood flow information combination unit 10 gives a larger weight as the number of analysis target data items included in each of the plurality of division sections becomes larger and adds a plurality of blood flow information items to combine the blood flow information items.

The case in which the MTI filter unit 8 changes the predetermined filter characteristics such that the amount of attenuation of the low-frequency component of the analysis target data becomes larger as the relative movement distance of the scatterer becomes longer in Step S4 has been described above. However, in a case in which the relative movement distance of the scatterer is less than a predetermined value, the MTI filter unit 8 may change the predetermined filter characteristics such that the amount of attenuation of the low-frequency component of the analysis target data is reduced.

In addition, the MTI filter unit 8 may calculate a correlation matrix in a predetermined range in the range over a plurality of scanning lines based on the analysis target data and perform principal component analysis having clutter as a main component to remove clutter components from a plurality of analysis target data items. In this case, first, the MTI filter unit 8 calculates the average value of the correlation matrix in a predetermined range in the range over a plurality of scanning lines based on the analysis target data. For example, in the technique disclosed in JP2014-158698A, the average value of the correlation matrix represented by the following Expression (1) is used.

[Expression 1]

$$R_{xx} = \frac{1}{M} \sum_{m=1}^{M} x_m x_m^H \quad (1)$$

Here, in Expression (1), $x_m$ is a column vector indicating a time-series data string at a point m included in a predetermined range and M is the total number of points m included in a predetermined range. In addition, $x_m^H$ is a complex conjugate of a row vector obtained by transposing $x_m$.

The predetermined range may be the entire scanning range over a plurality of scanning lines and is desirably determined as a region of interest in the vicinity of the analysis target data. Specifically, the vicinity of the analysis target data is a two-dimensional range including a plurality of scanning lines and a depth range in the vicinity of the analysis target data or a one-dimensional range which is a depth range in the vicinity of the analysis target data. In addition, the predetermined range may be determined as a range obtained by excluding the analysis target data from the region in the vicinity of the analysis target data, in order to remove the influence of the blood flow signal included in the analysis target data.

In Embodiment 1 according to the invention, the MTI filter unit 8 can use only the time-series data of the point m whose movement distance is equal to or less than a threshold value in a plurality of extracted data items for the calculation of the correlation matrix. In this case, for example, the MTI filter unit 8 can calculate the correlation matrix using the following Expression (2).

[Expression 2]

$$R_{xx} = \frac{\sum_{m=1}^{M} W_m x_m x_m^H}{M \sum_{m=1}^{M} W_m} \quad (2)$$

Here, in Expression (2), $W_m$ is a weighting value at the point m, is 0 in a case in which the movement distance of the point m is greater than the threshold value, and is 1 in a case in which the movement distance of the point m is equal to or less than the threshold value. As such, in a case in which the average value of the correlation matrix is calculated, the MTI filter unit 8 can exclude the point whose movement distance is long, that is, the point with low correlation in the extracted data items that are adjacent to each other in time series. Therefore, in a case in which principal component analysis is performed, it is possible to improve the accuracy of estimating clutter.

Embodiment 2

In the blood flow information acquisition operation according to Embodiment 1, the ultrasound diagnostic apparatus 1 estimates the movement distance of the scatterer included in the extracted data items which are adjacent to each other in time series and selects analysis target data on the basis of the movement distance of the scatterer. Here, for example, even though each of a plurality of movement distances estimated for the scatterer is a small value, the finally integrated movement distance of the scatterer is large in a case in which the movement directions of the scatterer corresponding to the movement distances are the same. Therefore, the correlation between the first data and the last data in the time-series data is reduced. In order to solve the problem, the ultrasound diagnostic apparatus 1 may calculate the analysis target data, considering the direction of the motion vector of the scatterer in addition to the movement distance of the scatterer.

Figure 11:
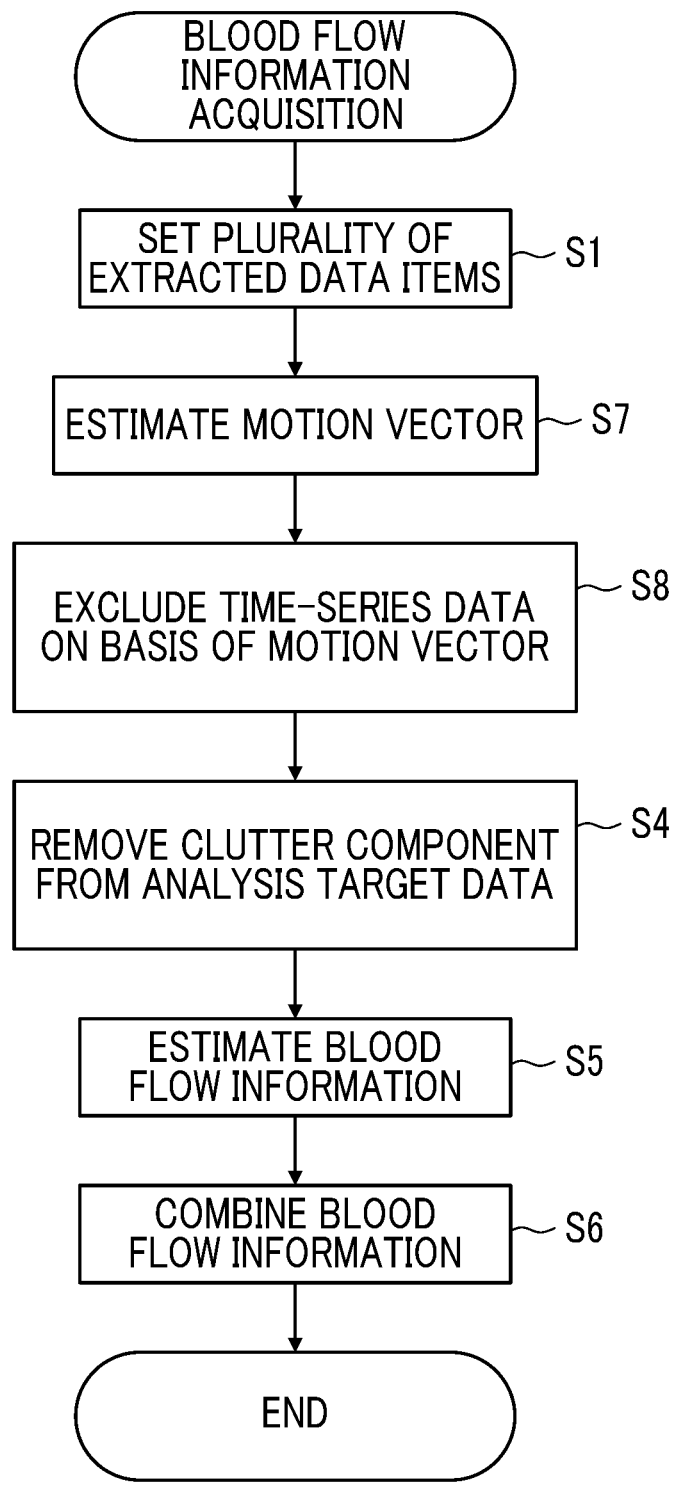
FIG. 11 is a flowchart illustrating a blood flow information acquisition operation of an ultrasound diagnostic apparatus according to Embodiment 2 of the invention.

FIG. 11 illustrates a blood flow information acquisition operation of an ultrasound diagnostic apparatus according to Embodiment 2. Here, the ultrasound diagnostic apparatus according to Embodiment 2 has the same configuration as the ultrasound diagnostic apparatus 1 according to Embodiment 1 illustrated in FIG. 1. In addition, since Step S1 and Steps S4 to S6 in a flowchart illustrated in FIG. 11 are the same as Step S1 and Steps S4 to S6 in the flowchart illustrated in FIG. 5, respectively, the detailed description of these steps will not be repeated.

In a case in which a plurality of extracted data items are set from a time-series data string in Step S1, the positional deviation amount estimation unit 22 of the analysis target data selection unit 7 estimates a motion vector of a scatterer included in the extracted data items which are adjacent to each other in time series in Step S7. A method for estimating the motion vector of the scatterer is the same as the method in Embodiment 1.

Then, in Step S8, the data exclusion unit 23 of the analysis target data selection unit 7 excludes time-series data from the time-series data string on the basis of the motion vector of the scatterer estimated in Step S7 and selects analysis target data. Step S8 will be described in detail with reference to a flowchart illustrated in FIG. 12.

Figure 12:
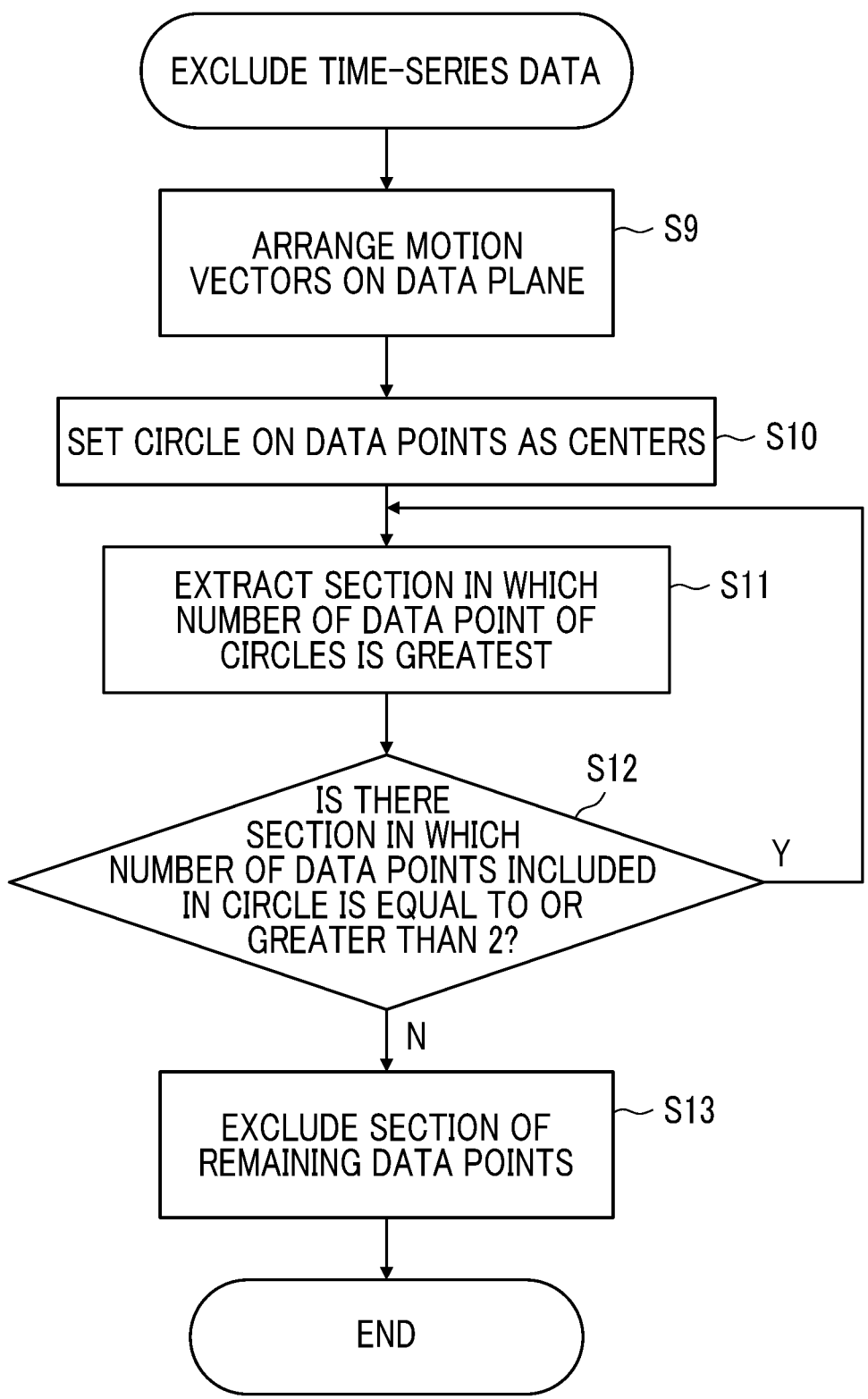
FIG. 12 is a flowchart illustrating a time-series data exclusion operation in Embodiment 2 of the invention.

The time-series data exclusion operation in Step S8 includes Steps S9 to S13 as illustrated in FIG. 12.

Figure 13:
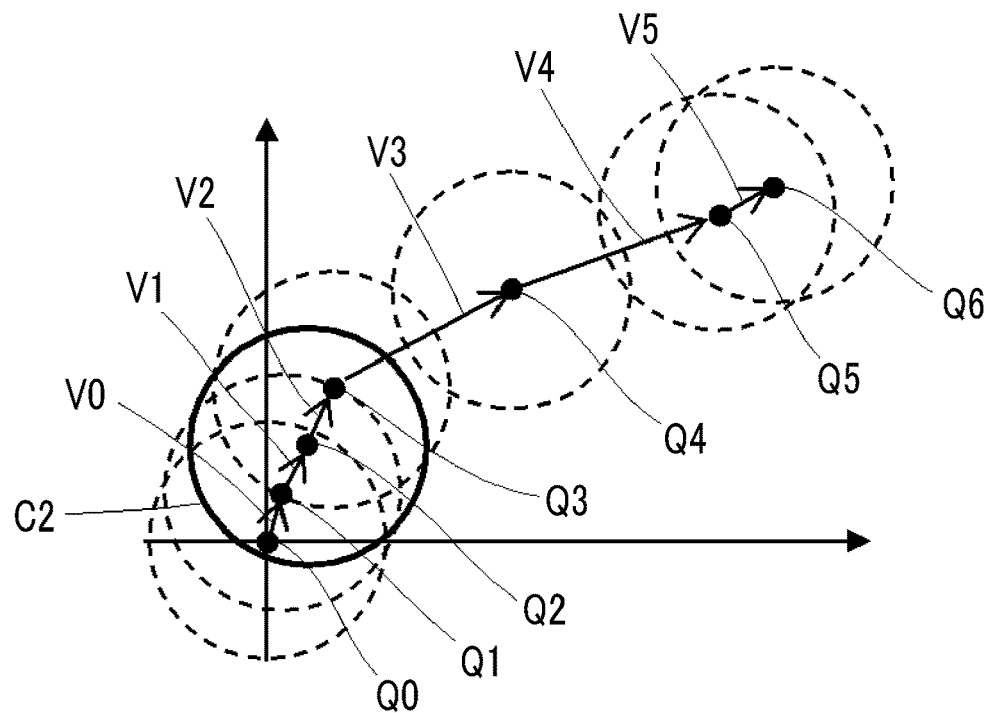
FIG. 13 is a conceptual diagram illustrating an example of a plurality of motion vectors arranged on a data plane.

First, in Step S9, the data exclusion unit 23 arranges a plurality of motion vectors of the scatterer included in the plurality of extracted data items on a data plane in time series. In this case, the data exclusion unit 23 sequentially connects starting points and end points of the plurality of motion vectors in time series. As a result, as illustrated in FIG. 13, a plurality of data points corresponding to the starting points and the end points of the plurality of motion vectors are arranged on the data plane. In FIG. 13, motion vectors V0 to V5 are arranged on a data plane DP and data points Q0 to Q6 corresponding to the starting points and the end points of the motion vectors V0 to V5 are arranged. The data points Q0 to Q6 are points corresponding to extracted data items arranged in time series.

Then, in Step S10, the data exclusion unit 23 sets circles which have the same radius and have the plurality of data points arranged on the data plane as the centers. The radii of the plurality of circles can be set to a predetermined value in advance.

In Step S11, the data exclusion unit 23 specifies a circle including the largest number of data points that are continuous in time series among the plurality of circles having each data point as the center. Then, the data exclusion unit 23 selects a section of a plurality of data points included in the specified circle, that is, a plurality of time-series data items in the range of a plurality of extracted data items corresponding to the plurality of data points as the analysis target data. In the example illustrated in FIG. 13, among a plurality of circles having the data points Q0 to Q6 as the centers, a circle C2 having the data point Q2 as the center includes the largest number of data points that are continuous in time series and a section of four data points Q0 to Q3 included in the circle C2 is extracted as the analysis target data.

Figure 14:
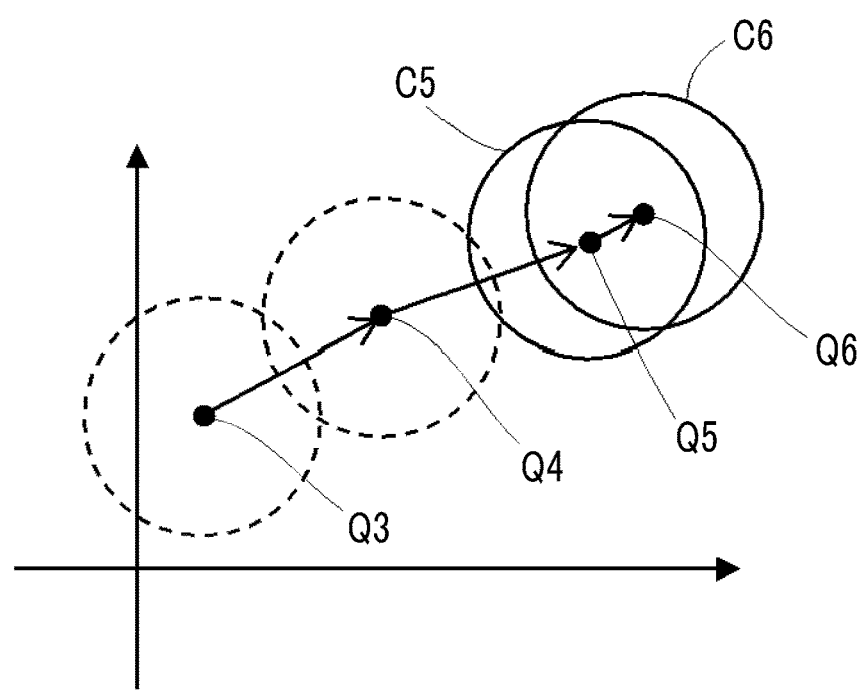
FIG. 14 is a conceptual diagram illustrating an example of a motion vector that remains as a result of the extraction of a plurality of data points from the data plane.

In a case in which the section of a plurality of data points is extracted as the analysis target data in Step S11, in Step S12, the data exclusion unit 23 determines whether there is a section in which the number of data points included in one of a plurality of circles having the remaining data points as the centers is equal to or greater than 2. For example, in a case in which the section of the data points Q0 to Q3 illustrated in FIG. 13 is extracted as the analysis target data, a section of the data points Q3 to Q6 remains as illustrated in FIG. 14. In the example illustrated in FIG. 14, circles C5 and C6 which have the data points Q5 and Q6 as the centers, respectively, include the two data points Q5 and Q6. As such, in a case in which there is a section in which the number of data points included in a circle is equal to or greater than 2, the process returns to Step S11.

In a case in which the process returns to Step S11, the data exclusion unit 23 specifies a circle including the largest number of data points that are continuous in time series among a plurality of circles having the remaining data points as the centers and selects a section of a plurality of data points included in the specified circle as the analysis target data. In the example illustrated in FIG. 14, a section of the data points Q5 to Q6 included in the circles C5 and C6 is extracted as the analysis target data. In this case, as a result of the extraction of a plurality of data points as the analysis target data, the time-series data string is divided into a division section corresponding to the data points Q0 to Q3 and a division section corresponding to the data points Q5 and Q6. As such, as a result of the extraction of the section of a plurality of data points as the analysis target data, in some cases, the time-series data string is divided into a plurality of division sections.

As described above, in Steps S12 and S13, the data exclusion unit 23 sequentially extracts, as the analysis target data, the section of a plurality of data points which are continuous in time series in descending order of the number of data points. In a case in which there is no section in which the number of data points included in each circle having each data point as the center is equal to or greater than 2, the process proceeds to Step S13.

In a case in which there is a remaining data point as a result of the extraction of the section of the data points in Steps S11 and S12, in Step S13, the data exclusion unit 23 excludes the section of the remaining data points, that is, a plurality of time-series data items in the range of the extracted data corresponding to the data point included in only one circle from the Doppler analysis target.

Then, in a case in which the time-series data exclusion operation in Step S8 ends, in Step S4, clutter components are removed from a plurality of analysis target data items. Then, in Steps S5 and S6, blood flow information is estimated and combined. Then, the blood flow information acquisition operation according to Embodiment 2 ends.

In the blood flow information acquisition operation of the ultrasound diagnostic apparatus 1 according to Embodiment 2, a plurality of motion vectors of the scatterer included in the time-series data string are arranged on the data plane so as to be connected to each other in time series. Then, the sections of the data points corresponding to the starting points and the end points of each motion vector are sequentially selected as the analysis target data in descending order of the number of data items which are continuous in time series and are included in each circle having each data point as the center. Therefore, even in a case in which the tissues of the subject are largely moved in the same direction, the ultrasound diagnostic apparatus 1 can acquire blood flow information with high accuracy.

The case in which the radii of a plurality of circles set in Step S10 can be set to a predetermined value in advance has been described above. However, the radius may be set to a larger value as the wavelength with respect to the center frequency of the ultrasound beam transmitted to the scatterer becomes larger. Here, as the frequency of the ultrasound beam transmitted to the scatterer becomes higher, the granularity of a speckle pattern included in the time-series data string becomes finer and the resolution of each time-series data item becomes higher. In a time-series data string with high resolution, in a case in which the scatterer is relatively moved, the correlation between the time-series data items is likely to be lower than that in a time-series data string with low resolution. In a case in which Doppler analysis is performed, it is desirable to perform analysis for each section of a plurality of analysis target data items having a correlation equal to or higher than a predetermined value, in order to improve the accuracy of estimating the blood flow information. Therefore, it is desirable that the radius of a circle having, as the center, a data point corresponding to time-series data with low resolution is less than the radius of a circle having, as the center, a data point corresponding to time-series data with high resolution. Therefore, it is possible to set the radii of a plurality of circles set in Step S10 to a larger value as the center frequency of the ultrasound beam transmitted to the scatterer becomes lower, that is, as the wavelength with respect to the center frequency becomes larger. In addition, it is desirable to set the specific radius of a circle according to the performance of the filter in the MTI filter unit 8. In the MTI filter according to the related art, in a case in which the movement distance of the scatterer is larger than a wavelength corresponding to the center frequency of an ultrasonic beam, a clutter component is unlikely to be sufficiently suppressed. Therefore, for example, in a case in which an MTI filter having the same performance as the MTI filter according to the related art is used, it is desirable that the radius of the circle is set to one-half to one times the wavelength corresponding to the center frequency of the ultrasound beam.

Figure 15:
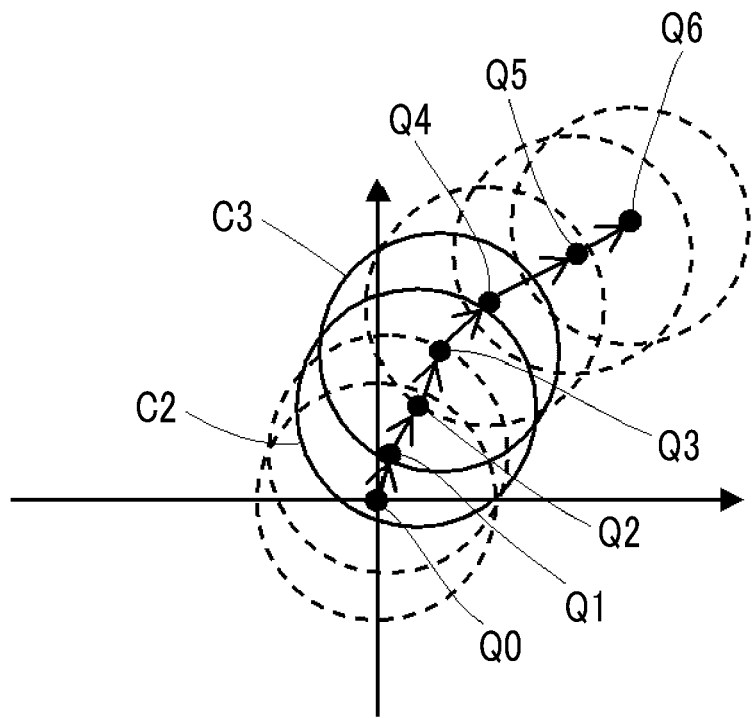
FIG. 15 is a conceptual diagram illustrating another example of a plurality of motion vectors arranged on the data plane.

Further, in a case in which the section of a plurality of data points is extracted as the analysis target data in Step S11, as illustrated in FIG. 15, there may be two or more circles including the largest number of data points which are continuous in time series and the circles may share the same data point. In the example illustrated in FIG. 15, a circle C2 includes four data points Q0 to Q3 and a circle C3 includes four data points Q1 to Q4. In addition, the circles C2 and C3 share three data points Q1 to Q3. In this case, it is desirable that the data exclusion unit 23 of the analysis target data selection unit 7 selects a section of a plurality of data points as the data analysis target such that a longer section of a plurality of data points that are continuous in time series remains. In the example illustrated in FIG. 15, in a case in which a section of the data points Q0 to Q3 included in the circle C2 is selected as the analysis target data, three data points Q4 to Q6 that are continuous in time series remain. In a case in which a section of the data points Q1 to Q4 included in the circle C3 is selected as the analysis target data, the remaining data points are divided into a section including only the data point Q0 and a section of two data points Q5 and Q6. Therefore, in this case, it is desirable to select the section of the data points Q0 to Q3 included in the circle C2 as the analysis target data.

Figure 16:
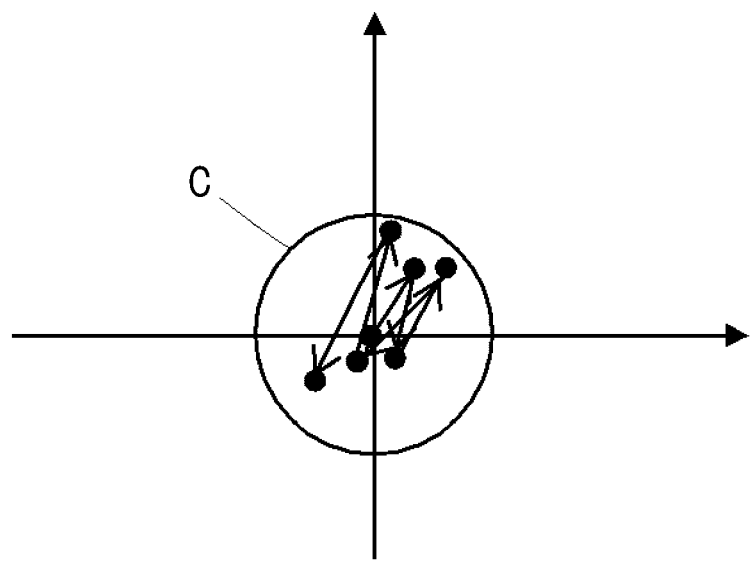
FIG. 16 is a conceptual diagram illustrating still another example of a plurality of motion vectors arranged on the data plane.

Further, in a case in which a plurality of circles are set in Step S10, a circle C including all data points may be set as illustrated in FIG. 16. In this case, for example, the scatterer included in the time-series data string can be considered to be reciprocating. Therefore, the net movement distance of the scatterer between the first data point and the last data point of the time-series data falls within the circle set in Step S10 and all of the values of the time-series data string are selected as the analysis target data.

In addition, in Embodiment 2, similarly to Embodiment 1, the MTI filter unit 8 may calculate a correlation matrix in a predetermined range having each corresponding point as the center in the range over a plurality of scanning lines and perform principal component analysis having a clutter as a main component to remove a clutter component from a plurality of analysis target data items.

In this case, for example, the positional deviation amount estimation unit of the analysis target data selection unit 7 estimates the motion vector of the scatterer, that is, a reference point included in the time-series data string and a plurality of neighboring displacement vectors having the relative movement distance and movement direction of each point other than the reference point as an absolute value and a direction. Then, the MTI filter unit 8 gives a larger weight to a plurality of analysis target data items as the correlation between the motion vector of the reference point and the plurality of neighboring displacement vectors becomes higher in a predetermined range and calculates the average value of the correlation matrix with respect to the plurality of analysis target data items. Expression (2) in Embodiment 1 can be used as an expression indicating the average value of the correlation matrix calculated by the MTI filter unit 8. In Embodiment 2, the following Expression (3) can be used as a weighting value $W_j$ for a point where m=j is established in Expression (2).

[Expression 3]

$$W_j = \frac{\frac{V_j \cdot V_i}{|V_j||V_i|} + 1}{2} \quad (3)$$

Here, in Expression (3), $V_i$ indicates a motion vector of a point i included in a time-series data string and $V_j$ indicates a neighboring displacement vector of each point j in a predetermined range having the point i as the center. In addition, $V_j \cdot V_i$ indicates the inner product of the motion vector $V_i$ and the neighboring displacement vector $V_j$ and $|V_i|$ and $|V_j|$ indicate the absolute value of the motion vector $V_i$ and the absolute value of the neighboring displacement vector $V_j$, respectively. As such, in Embodiment 2, the MTI filter unit 8 calculates the average value of the correlation matrix such that a weighting value becomes larger as the direction of each neighboring displacement vector becomes closer to the direction of the motion vector of the reference point. Therefore, it is possible to reduce the influence of a point with low correlation and to improve the accuracy of estimating clutter.

Embodiment 3

In some cases, the time-series data string acquired in Embodiment 1 and Embodiment 2 includes the time-series data items having a low similarity therebetween. For example, the similarity is reduced in a case in which the tissues of the subject are moved in a direction perpendicular to an array surface of a transducer array of an ultrasound probe and a case in which the pattern of ultrasound echoes is changed in a complicated manner by the flow of a very small scatterer, such as a red blood cell, at the point where an ultrasound beam is reflected. As such, in a case in which the time-series data string includes the time-series data items having a low similarity therebetween, it is desirable to change the characteristics of a filter for removing a clutter component from the analysis target data to appropriate characteristics according to time-series data.

Figure 17:
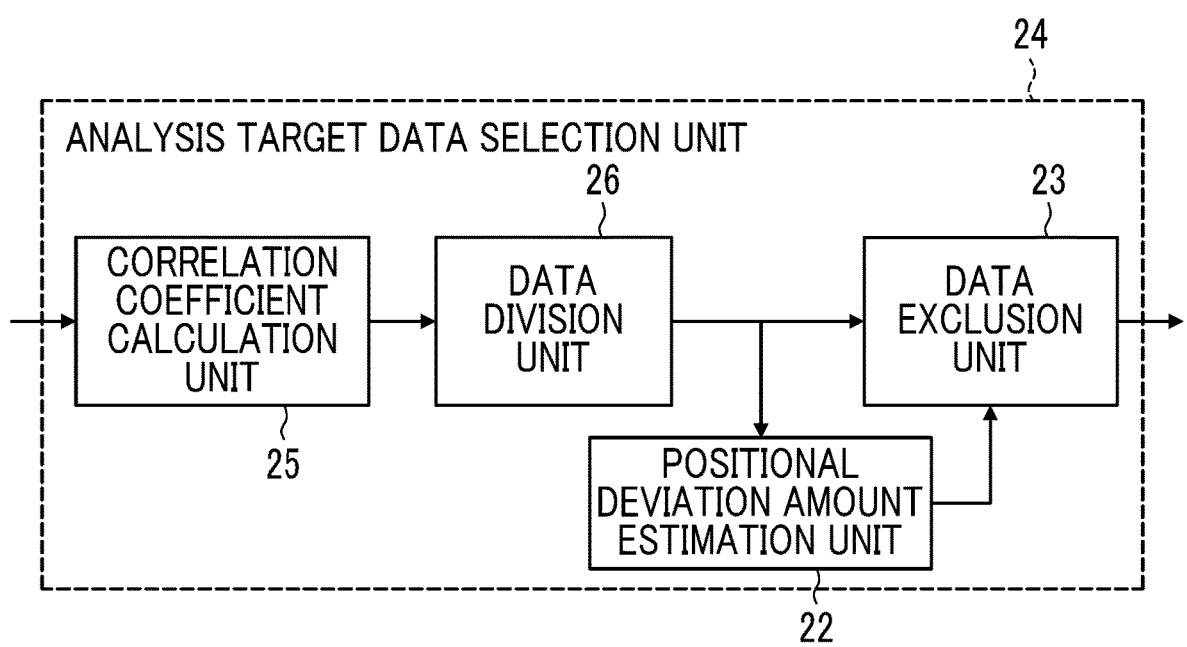
FIG. 17 is a block diagram illustrating the internal configuration of an analysis target data selection unit in Embodiment 3 of the invention.

An ultrasound diagnostic apparatus according to Embodiment 3 has the same configuration as the ultrasound diagnostic apparatus 1 according to Embodiment 1 except that it includes an analysis target data selection unit 24 illustrated in FIG. 17 instead of the analysis target data selection unit 7 of the ultrasound diagnostic apparatus 1 according to Embodiment 1 illustrated in FIG. 1.

The analysis target data selection unit 24 includes a correlation coefficient calculation unit 25, a data division unit 26, a positional deviation amount estimation unit 22, and a data exclusion unit 23. In addition, the data division unit 26 is connected to the correlation coefficient calculation unit 25 and the data exclusion unit 23 is connected to the data division unit 26. Further, the positional deviation amount estimation unit 22 is connected to the data division unit 26.

The positional deviation amount estimation unit 22 and the data exclusion unit 23 of the analysis target data selection unit 24 are the same as the positional deviation amount estimation unit 22 and the data exclusion unit 23 of the analysis target data selection unit 7 illustrated in FIG. 4 in Embodiment 1, respectively.

The correlation coefficient calculation unit 25 calculates a correlation coefficient in the same region of interest in time-series data items acquired at different points of time among a plurality of time-series data items forming the time-series data string. Here, the correlation coefficient is an index indicating the similarity of one time-series data item to the other time-series data item. A larger correlation coefficient indicates a higher similarity between two time-series data items. In addition, the correlation coefficient calculation unit 25 can calculate the correlation coefficient between the time-series data items using the method according to the related art.

The data division unit 26 divides the time-series data string into a plurality of data groups according to the correlation coefficient between the time-series data items calculated by the correlation coefficient calculation unit 25. In addition, the data division unit 26 can further divide the time-series data items classified into the plurality of data groups on the basis of the amount of change in a brightness value between a plurality of time-series data items, which will be described in detail below.

Figure 18:
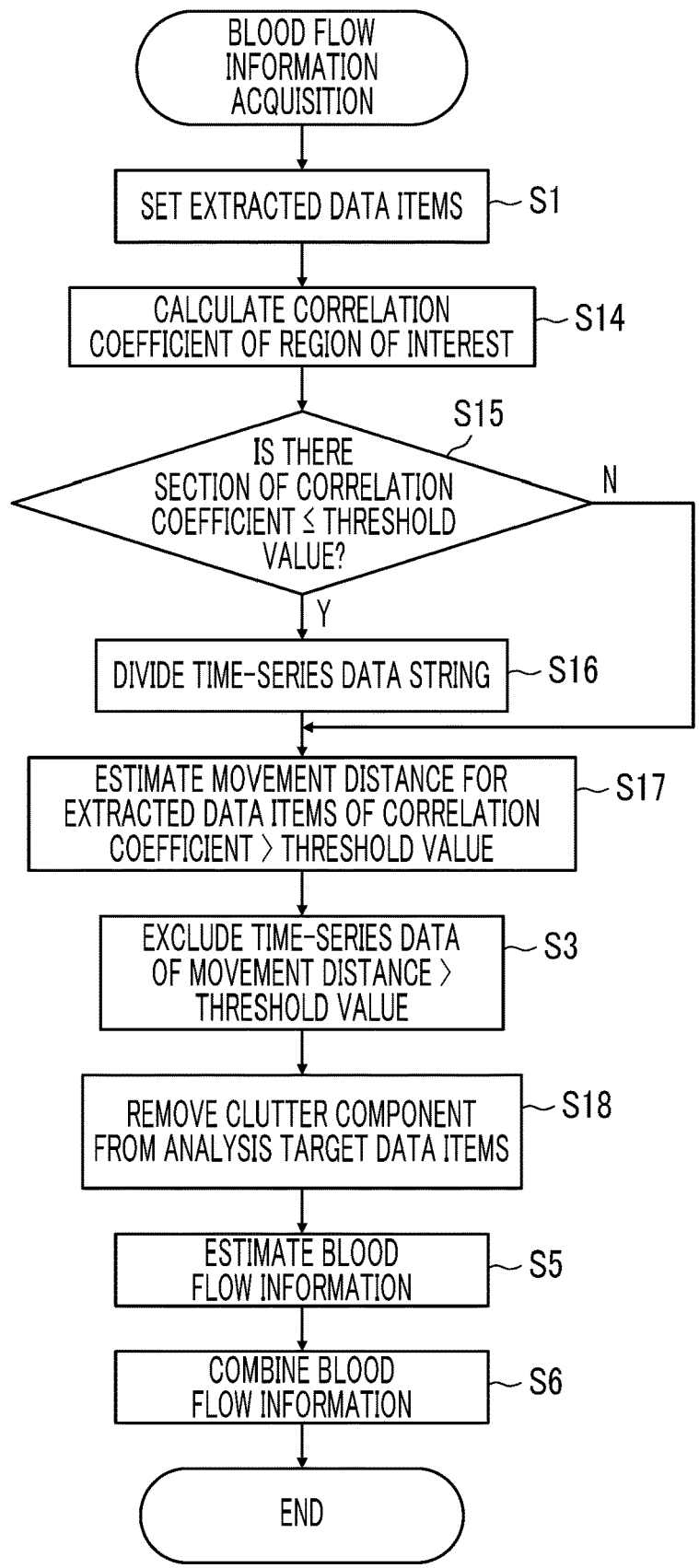
FIG. 18 is a flowchart illustrating a blood flow information acquisition operation in Embodiment 3 of the invention.

FIG. 18 illustrates a flowchart illustrating a blood flow information acquisition operation according to Embodiment 3. In the flowchart, since Step S1, Step S3, Step S5, and Step S6 are the same as Step S1, Step S3, Step S5, and Step S6 in Embodiment 1 illustrated in FIG. 5, the detailed description thereof will not be repeated.

First, in a case in which a plurality of extracted data items are set from a time-series data string in Step S1, the process proceeds to Step S14.

In Step S14, the correlation coefficient calculation unit 25 of the analysis target data selection unit 24 calculates a correlation coefficient in the same region of interest based on the corresponding points for a plurality of extracted data items which are adjacent to each other in time series.

Then, in Step S15, the data division unit 26 of the analysis target data selection unit 24 determines whether there is a correlation coefficient equal to or less than a predetermined threshold value among a plurality of correlation coefficients calculated in Step S14. This is to divide the time-series data string according to the value of the correlation coefficient. In a case in which it is determined in Step S15 that there is a correlation coefficient equal to or less than the threshold value, the process proceeds to Step S16.

Figure 19:
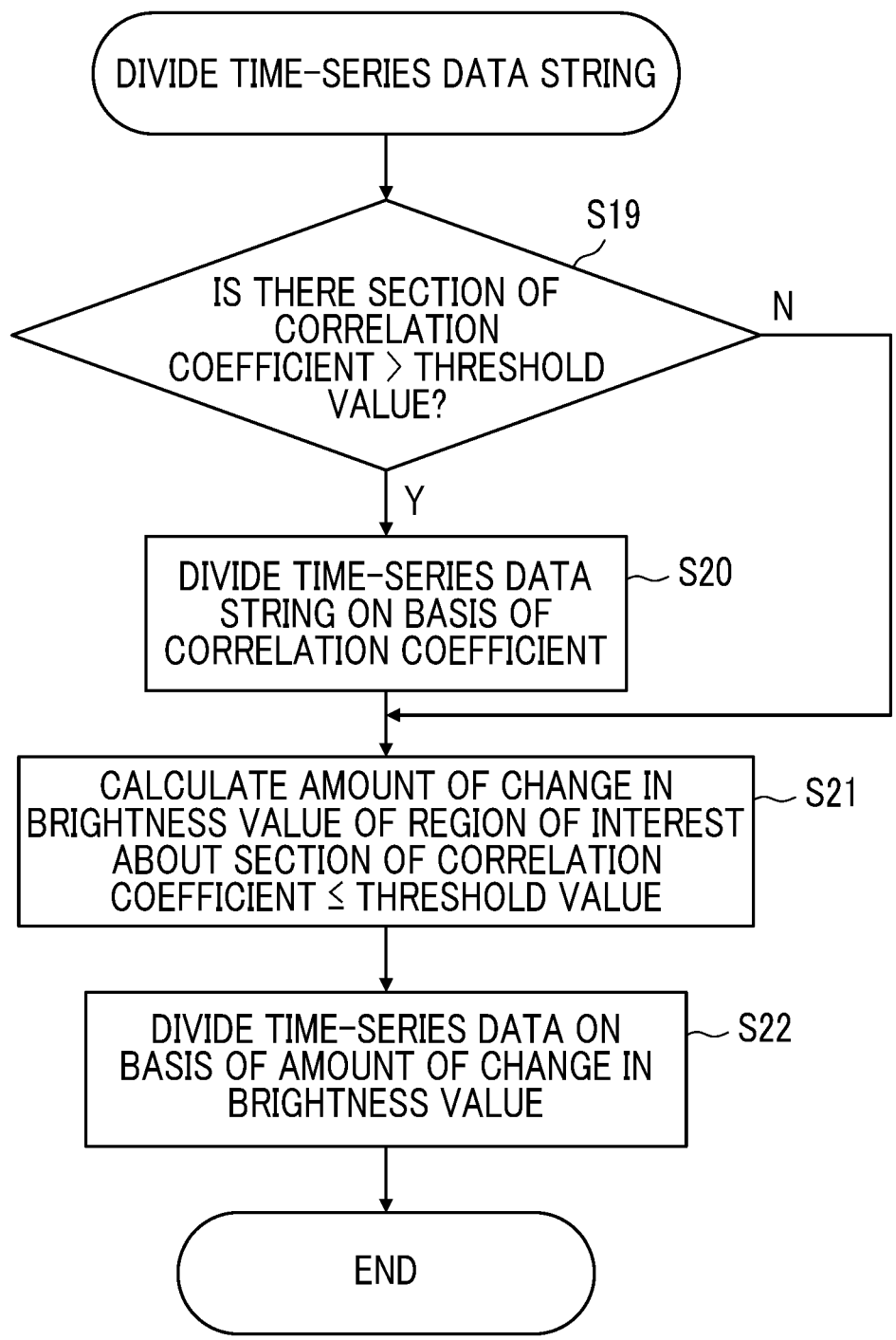
FIG. 19 is a flowchart illustrating a time-series data string division operation in Embodiment 3 of the invention.

In Step S16, the data division unit 26 divides the time-series data string into a plurality of data groups on the basis of the values of the plurality of correlation coefficients calculated in Step S14. Step S16 will be described in detail with reference to a flowchart illustrated in FIG. 19. As illustrated in FIG. 19, the time-series data string division operation illustrated in Step S16 includes Steps S19 to S22.

Figure 20:
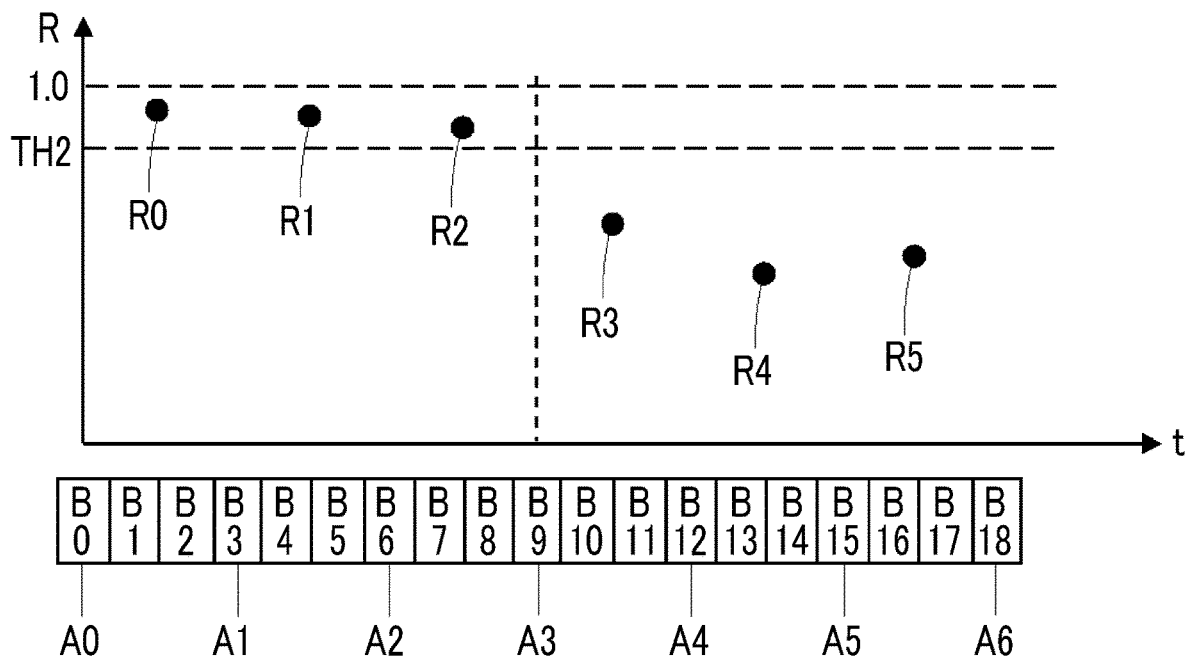
FIG. 20 is a diagram illustrating an example of a correlation coefficient of a region of interest in a plurality of extracted data items.

First, in Step S19, the data division unit 26 determines whether there is a time-series data section in which the correlation coefficient between a plurality of extracted data items is greater than the predetermined threshold value. The determination is performed in order to divide the time-series data string according to the value of the correlation coefficient in a case in which the plurality of correlation coefficients include a correlation coefficient greater than the threshold value and a correlation coefficient equal to or less than the threshold value. In a case in which it is determined in Step S19 that there is a time-series data section in which the correlation coefficient is greater than the threshold value as illustrated in FIG. 20, the process proceeds to Step S20. In the example illustrated in FIG. 20, R indicates a correlation coefficient, t indicates time, and TH2 indicates a threshold value determined for the correlation coefficient R. Here, the maximum value of the correlation coefficient R in FIG. 20 is 1.0. In addition, B0 to B18 indicate time-series data items forming a time-series data string and A0 to A6 indicate extracted data items. Further, R0 to R5 indicate correlation coefficients calculated from the extracted data items which are adjacent to each other in time series among the extracted data items A0 to A6. In FIG. 20, among the plurality of correlation coefficients R0 to R5, the correlation coefficients R0 to R2 are greater than the threshold value TH2.

In Step S20 following Step S19, the data division unit 26 divides the time-series data string into a first data group including the extracted data items whose correlation coefficient is greater than the threshold value and a second data group including the extracted data items whose correlation coefficient is equal to or less than the threshold value. In the example illustrated in FIG. 20, since the correlation coefficients R0 to R2 are greater than the threshold value TH2, the data division unit 26 specifies the time-series data items B0 to B8 in the range of the extracted data items A0 to A3 used to calculate the correlation coefficients R0 to R2 as the first data group. In addition, the data division unit 26 specifies the time-series data items B9 to B18 in the range of the extracted data items A3 to A6 used to calculate the correlation coefficients R3 to R5 which are equal to or less than the threshold value TH2 as the second data group. Here, the time-series data item B9 located at the boundary between the first data group and the second data group is assigned to the second data group in FIG. 20. However, the time-series data item B9 may be assigned to the first data group.

As such, in a case in which the time-series data string is divided into the first data group and the second data group in Step S20, the process proceeds to Step S21.

Figure 21:
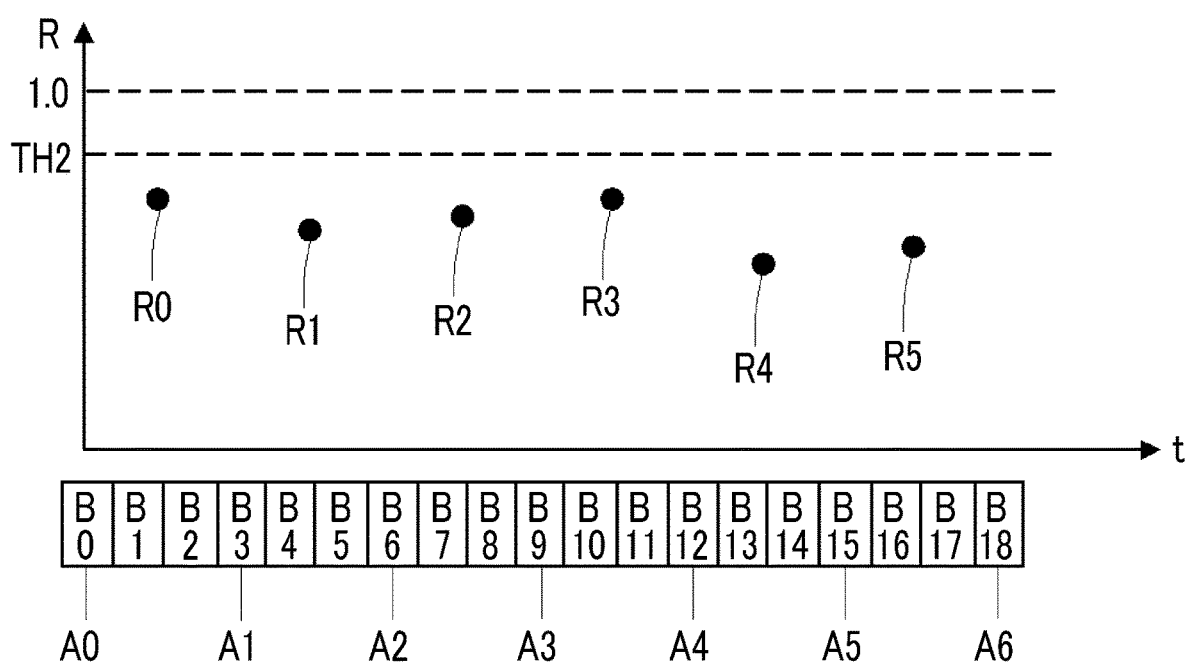
FIG. 21 is a diagram illustrating another example of the correlation coefficient of the region of interest in the plurality of extracted data items.

In a case in which it is determined in Step S19 that there is no time-series data section in which the correlation coefficient is greater than the threshold value as illustrated in FIG. 21, that is, that the correlation coefficient is equal to or less than the threshold value in all of the sections of the time-series data string, the process proceeds to Step S21 without passing through Step S20.

In Step S21 following Step S19 and Step S20, the data division unit 26 calculates the amount of change in a brightness value between the extracted data items which are adjacent to each other in time series in the time-series data section in which the correlation coefficient is equal to or less than the threshold value. This is to divide the time-series data items in which the correlation coefficient is equal to or less than the threshold value into a plurality of data groups according to the amount of change in the brightness value.

Here, for example, the correlation coefficient between the time-series data items is equal to or less than the threshold value due to the acquisition of the time-series data items for different tomographic planes or the acquisition of time-series data for the inside of the blood vessels. For example, in the acquisition of the time-series data, in a case in which the angle of the ultrasound probe with respect to the subject is changed and in a case in which the tissues of the subject are moved in a direction perpendicular to the tomographic plane, time-series data items for different tomographic planes are acquired. As such, since all of the time-series data items acquired for different tomographic planes change largely, the amount of change in brightness value between the time-series data items is likely to increase. For the time-series data items acquired for the inside of the blood vessels, the correlation coefficient is reduced by the movement of very small scatterers such as red blood cells. However the spatial average value of the amplitude of the time-series data does not change largely in a short time. Therefore, the amount of change in brightness value between the time-series data items is likely to be reduced. For this reason, time-series data items having a large amount of change in the brightness value therebetween can be determined to be the time-series data items acquired for different tomographic planes. In addition, time-series data items having a small amount of change in the brightness value therebetween can be determined to be the time-series data items acquired for the inside of the blood vessels. Therefore, it is desirable that filter characteristics for the time-series data items having a large amount of change in the brightness value therebetween are different from filter characteristics for the time-series data items having a small amount of change in the brightness value therebetween.

In addition, the data division unit 26 can calculate the amount of change in the brightness value between the extracted data items using various calculation methods. For example, the data division unit 26 can calculate, as the amount of change in the brightness value, the sum of squares of differences in the brightness values of the same region of interest having a corresponding point as the center for the extracted data items which are adjacent to each other in time series.

Figure 22:
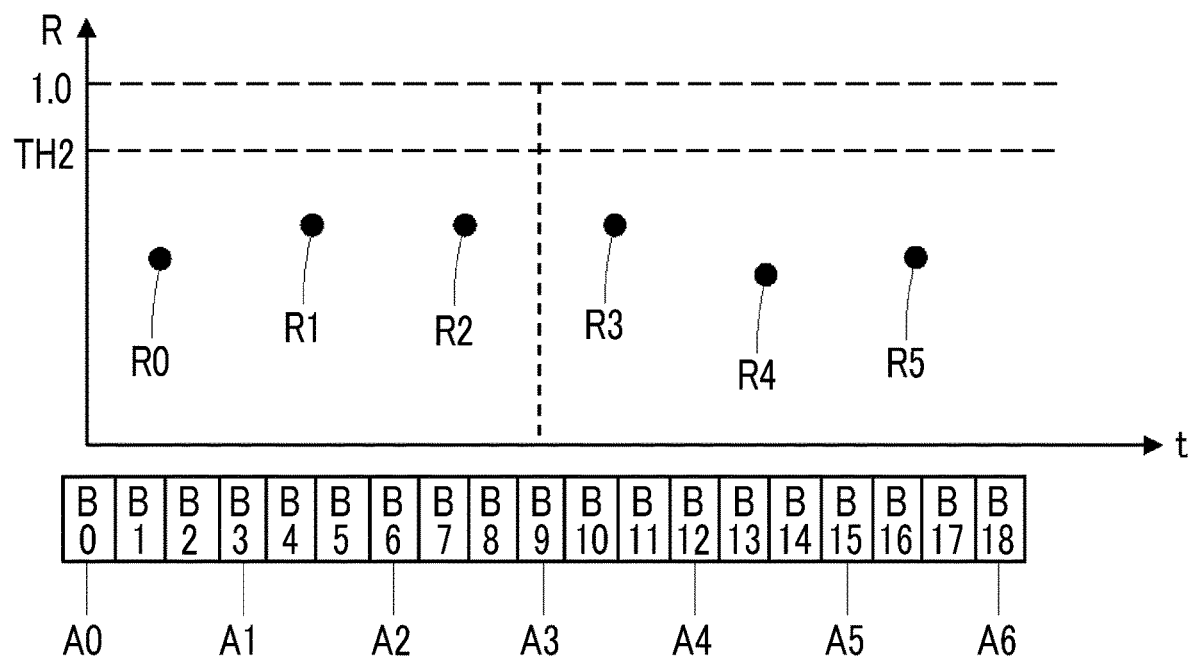
FIG. 22 is a diagram illustrating still another example of the correlation coefficient of the region of interest in the plurality of extracted data items.

Then, in Step S22, the data division unit 26 divides the time-series data section in which the correlation coefficient is equal to or less than the threshold value on the basis of the amount of change in the brightness value calculated in Step S21. In this case, as illustrated in FIG. 22, the data division unit 26 specifies a time-series data section in which the amount of change in the brightness value is equal to or less than a threshold value as a third data group and specifies a time-series data section in which the amount of change in the brightness value is greater than the threshold value as a fourth data group. In the example illustrated in FIG. 22, the amount of change in the brightness value calculated using the extracted data items A0 to A3 is equal to or less than the threshold value and the amount of change in the brightness value calculated using the extracted data items A3 to A6 is greater than the threshold value. In this case, the time-series data string is divided into the time-series data items B0 to B9 in the third data group and the time-series data items B10 to B18 in the fourth data group. Here, the time-series data B9 located at the boundary between the third data group and the fourth data group is assigned to the third data group in the example illustrated in FIG. 22. However, the time-series data B9 may be assigned to the fourth data group.

As such, the time-series data section in which the correlation coefficient is equal to or less than the threshold value is divided into the third data group and the fourth data group. In addition, the data division unit 26 selects the time-series data items having correlation coefficients equal to or less than the threshold value which have been divided into each data group as the analysis target data to be subjected to Doppler analysis for each divided data group.

Then, the time-series data string division operation in Step S16 ends.

In Step S17 following Step S16, the positional deviation amount estimation unit 22 of the analysis target data selection unit 24 estimates the relative movement distance of the scatterer included in a plurality of extracted data items for the extracted data items having correlation coefficients greater than the threshold value. A method for estimating the movement distance of the scatterer in Step S17 is the same as the method for estimating the movement distance of the scatterer in Step S2 of the flowchart illustrated in FIG. 5 in Embodiment 1.

Then, in Step S3, the data exclusion unit 23 of the analysis target data selection unit 24 specifies extracted data items in which the estimated movement distance of the scatterer is greater than the threshold value, excludes a plurality of time-series data items in the range of the extracted data items, and selects the remaining time-series data items as the analysis target data.

In Step S18 following Step S3, the data exclusion unit 23 removes a clutter component from the remaining analysis target data items obtained by excluding time-series data from a plurality of time-series data items having correlation coefficients greater than the threshold value on the basis of the movement distance of the scatterer and removes a clutter component from a plurality of analysis target data items having correlation coefficients equal to or less than the threshold value which have been divided in Step S16. A filtering method for the analysis target data items having correlation coefficients greater than the threshold value is the same as the filtering method described in Step S4 of the flowchart illustrated in FIG. 5.

For the filtering process for the analysis target data items having correlation coefficients equal to or less than the threshold value in Step S18, it is desirable that a filtering method for the analysis target data items divided as the third data group is different from a filtering method for the analysis target data items divided as the fourth data group. The MTI filter unit 8 determines that the analysis target data items divided as the third data group among the analysis target data items having correlation coefficients equal to or less than the threshold value are the analysis target data items acquired for the inside of the blood vessels and changes the predetermined filter characteristics such that the amount of attenuation of low-frequency components is reduced. In addition, the MTI filter unit 8 determines that the analysis target data items divided as the fourth data group among the analysis target data items having correlation coefficients equal to or less than the threshold value are the analysis target data items acquired for different tomographic planes and changes the predetermined filter characteristics such that the amount of attenuation of low-frequency components increases.

In a case in which clutter components are removed from a plurality of analysis target data items by the filtering process performed for the plurality of analysis target data items in Step S18, in Step S5, blood flow information items are estimated for a plurality of division sections and each data group. In Step S6, the plurality of blood flow information items are combined with each other.

Then, the blood flow information acquisition operation according to Embodiment 3 ends.

In the above-mentioned blood flow information acquisition operation according to Embodiment 3, before a plurality of time-series data items are excluded from a time-series data string on the basis of the amount of relative positional deviation of the scatterer in the time-series data string, the time-series data string is divided into a plurality of data groups on the basis of the correlation coefficient between the extracted data items. Therefore, in Doppler analysis, it is possible to exclude the influence of the large amount movement of the tissues of the subject and to perform an appropriate filtering process according to analysis target data. Therefore, it is possible to obtain blood flow information with high accuracy.

In a case in which the amount of change in the brightness value of the same region of interest is calculated for the extracted data items which are adjacent to each other in time series in Step S21, it is desirable that the correlation coefficient calculation unit 25 of the analysis target data selection unit 24 performs a smoothing process for each of the extracted data items. This is to remove the influence of a speckle pattern included in the extracted data and the smoothing process is performed for an extraction pattern to improve the accuracy of the calculated amount of change in the brightness value.

The case in which the data division unit 26 calculates the sum of squares of differences in the brightness values of the same region of interest for the extracted data items which are adjacent to each other in time series has been described above. However, the amount of change in the brightness value may be calculated by other calculation methods. For example, the data division unit 26 may compare the average values of the brightness values of the same region of interest in the extracted data items which are adjacent to each other in time series to calculate the amount of change in the brightness value. Here, for example, in a case in which the average values of the brightness values are compared, the data division unit 26 can calculate the difference between the average values of the brightness values of the same region of interest in the extracted data items and can calculate the ratio of the average values of the brightness values.

In a case in which all of the correlation coefficients calculated in Step S14 is equal to or less than the threshold value as illustrated in FIG. 21, the data division unit 26 may determine that all of the time-series data items forming the time-series data string are the time-series data items acquired for the inside of the blood vessels and may specify all of the time-series data items as the third data group.

Further, the data exclusion unit 23 of the analysis target data selection unit 24 may exclude a plurality of time-series data items divided as the fourth data group in Step S22 from the analysis target data. The plurality of time-series data items divided as the fourth data group are determined to include the time-series data items acquired for tomographic planes different from the tomographic planes included in a plurality of time-series data items having correlation coefficients greater than the threshold value. Therefore, in some cases, the plurality of time-series data items divided as the fourth data group have a section that does not include a sufficient number of time-series data items to estimate blood flow information, which have been acquired in time series for the same tomographic plane. In this case, the contribution of the blood flow information estimated from the fourth data group to the combined blood flow information may be very small. Therefore, it is possible to reduce the calculation load of the ultrasound diagnostic apparatus for obtaining blood flow information by excluding the time-series data in the fourth data group from the analysis target data.

In addition, the data exclusion unit 23 can exclude, from the analysis target data items, the time-series data items, whose number is less than the predetermined number of data items and which are continuous in time series, among a plurality of time-series data items divided into a plurality of data groups by the data division unit 26. Here, in a case in which Doppler analysis is performed for the time-series data items whose number is less than the predetermined number of data items, the filter performance of the MTI filter unit 8 is not sufficiently exhibited and the accuracy of estimating blood flow information is likely to be reduced. For example, it is desirable to perform Doppler analysis for four or more time-series data items in order to prevent the reduction in the accuracy of estimating blood flow information. That is, it is preferable that the data exclusion unit 23 excludes three or less time-series data items which are continuous in time series from the analysis target data items. In this case, it is possible to improve the accuracy of estimating blood flow information.

The blood flow information acquisition operation according to Embodiment 3 corresponds to a blood flow information acquisition operation obtained by applying the process of dividing the time-series data string using the correlation coefficient of the region of interest to the blood flow information acquisition operation according to Embodiment 1. However, the process of dividing the time-series data string using the correlation coefficient of the region of interest, which is a feature of Embodiment 3, can also be applied to the blood flow information acquisition operation according to Embodiment 2. That is, the ultrasound diagnostic apparatus according to the invention may perform the process of dividing the time-series data string using the correlation coefficient of the region of interest before selecting the analysis target data on the basis of the motion vector of the scatterer in the time-series data string.

In Embodiment 3, similarly to Embodiment 1 and Embodiment 2, the MTI filter unit 8 may calculate a correlation matrix in a predetermined range having each corresponding point as the center in the range over a plurality of scanning lines and perform principal component analysis having clutter as a main component to remove clutter components from a plurality of analysis target data items.

In this case, for example, the MTI filter unit 8 can calculate the average value of the correlation matrix for the analysis target data in which the correlation coefficient of the region of interest is greater than the threshold value, using the method described in Embodiment 1. However, weighting may be performed for the analysis target data in which the correlation coefficient of the region of interest is equal to or less than the threshold value such that a small weight is given to a point with a small correlation coefficient and the average value of the correlation matrix may be calculated. That is, for the analysis target data in which the correlation coefficient of the region of interest is equal to or less than the threshold value, the average value of the correlation coefficient can be calculated by Expression (1) in Embodiment 1. The correlation coefficient at the point where m=i is established can be used as the weighting value $W_i$. In a case in which the weighting value is set in this way and principal component analysis is performed, it is possible to reduce the influence of a point with low correlation and to improve the accuracy of estimating clutter.

EXPLANATION OF REFERENCES

1: ultrasound diagnostic apparatus
2: ultrasound probe
2A: transducer array
3: data acquisition unit
4: receiving unit
5: transmitting unit
6: image generation unit
7, 24: analysis target data selection unit
8: MTI filter unit
9: blood flow information estimation unit
10: blood flow information combination unit
11: display control unit
12: display unit
13: apparatus control unit
14: operation unit
15: storage unit
16: amplification unit
17: A/D conversion unit
18: reception beam former
19: quadrature detection circuit
20: B-mode processing unit
21: image processing unit
22: positional deviation amount estimation unit
23: data exclusion unit
25: correlation coefficient calculation unit
26: data division unit
A0 to A6: extracted data
B0 to B18: time-series data
C, C2, C3, C5, C6: circle
D: search region
DP: data plane
L, L0 to L5: movement distance
O1, O2: region of interest
P1, P2: point of interest
Q0 to Q6: data point
R, R0 to R5: correlation coefficient
S: scatterer
TH1, TH2: threshold value
V, V0 to V5: motion vector
WF1, WF2, WF3: filter waveform
f: frequency
F(f): amount of attenuation
t: time

What is claimed is:

1. An ultrasound diagnostic apparatus comprising:
an ultrasound probe;
a transmission circuit configured to repeatedly transmit an ultrasound beam from the ultrasound probe to a subject a plurality of times in a range over a plurality of scanning lines
a reception circuit configured to receive reflected waves from the subject by the ultrasound probe to acquire a time-series data string of the reflected waves; and
a processor configured to estimate an amount of relative positional deviation of a scatterer of the subject which is included in the time-series data string, exclude, from the time-series data string, time-series data satisfying an exclusion condition based on the amount of positional deviation of the scatterer thus estimated to select analysis target data, remove a clutter component from the analysis target data thus selected, and analyze the analysis target data from which the clutter component has been removed to estimate blood flow information of the subject.

2. The ultrasound diagnostic apparatus according to claim 1,
wherein the processor estimates a relative movement distance of the scatterer on the basis of the time-series data string and excludes, from the time-series data string, a plurality of time-series data items in which the movement distance of the scatterer thus estimated is greater than a predetermined threshold value.

3. The ultrasound diagnostic apparatus according to claim 1,
wherein the processor sets a plurality of extracted data items which have been extracted at an interval of a predetermined number of data items in the time-series data string, estimates the relative movement distance of the scatterer for the plurality of extracted data items, and excludes, from the time-series data string, a plurality of time-series data items in a range of the plurality of extracted data items in which the movement distance of the scatterer thus estimated is greater than a predetermined threshold value.

4. The ultrasound diagnostic apparatus according to claim 2,
wherein the processor changes filter characteristics for the analysis target data in which the movement distance of the scatterer has been estimated such that, as the movement distance of the scatterer becomes longer, an amount of attenuation of a low-frequency component becomes larger.

5. The ultrasound diagnostic apparatus according to claim 3,
wherein the processor changes filter characteristics for the analysis target data in which the movement distance of the scatterer has been estimated such that, as the movement distance of the scatterer becomes longer, an amount of attenuation of a low-frequency component becomes larger.

6. The ultrasound diagnostic apparatus according to claim 2,
wherein the processor calculates an average value of a correlation matrix of the analysis target data in a predetermined range in the range over the plurality of scanning lines and performs principal component analysis having clutter as a main component, using the average value of the correlation matrix, to remove the clutter component from the analysis target data.

7. The ultrasound diagnostic apparatus according to claim 1,
wherein the processor estimates a motion vector which has a relative movement distance and a movement direction of the scatterer included in the time-series data as an absolute value and a direction, respectively, sequentially connects starting points and end points of a plurality of the motion vectors estimated from the time-series data string in time series, arranges data points corresponding to a plurality of time-series data items included in the time-series data string on a data plane, sequentially extracts a section of a plurality of the data points, which are continuous in time series and are included in any one of a plurality of circles that have the plurality of data points as centers and have the same radius, as the analysis target data in descending order of the number of data points, and excludes time-series data corresponding to the data point included in only one circle.

8. The ultrasound diagnostic apparatus according to claim 1,
wherein the processor sets a plurality of extracted data items which have been extracted at an interval of a predetermined number of data items in the time-series data string, estimates a motion vector which has a relative movement distance and a movement direction of the scatterer as an absolute value and a direction, respectively, for each of the plurality of extracted data items, sequentially connects starting points and end points of a plurality of the motion vectors estimated from the plurality of extracted data items in time series, arranges data points corresponding to the extracted data items on a data plane, sequentially extracts a section of a plurality of the data points, which are continuous in time series and are included in any one of a plurality of circles that have the plurality of data points as centers and have the same radius, as the analysis target data in descending order of the number of data points, and excludes time-series data corresponding to the data point included in only one circle.

9. The ultrasound diagnostic apparatus according to claim 7,
wherein the processor changes filter characteristics for a plurality of the analysis target data items corresponding to each extracted section of the plurality of data points such that, as a total sum of lengths of the motion vectors included in the section becomes larger, an amount of attenuation of a low-frequency component becomes larger.

10. The ultrasound diagnostic apparatus according to claim 7,
wherein the processor estimates a plurality of neighboring displacement vectors which have relative movement distances and movement directions of points included in the time-series data string in the range over the plurality of scanning lines as absolute values and directions, respectively, gives a larger weight to a plurality of the analysis target data items as a correlation between the motion vector and each of the neighboring displacement vectors becomes higher, calculates an average value of a correlation matrix for a plurality of the analysis target data items in a predetermined range in the range over the plurality of scanning lines, and performs principal component analysis having clutter as a main component, using the average value of the correlation matrix, to remove the clutter component from the remaining analysis target data items.

11. The ultrasound diagnostic apparatus according to claim 1,
wherein the processor calculates a correlation coefficient in the same region of interest in the time-series data string and divides the time-series data string into a first data group including time-series data items whose correlation coefficient is greater than a predetermined value, and a second data group including time-series data items whose correlation coefficient is equal to or less than the predetermined value.

12. The ultrasound diagnostic apparatus according to claim 11,
wherein the processor sets filter characteristics such that filter characteristics for the time-series data items in the first data group are different from filter characteristics for the time-series data items in the second data group.

13. The ultrasound diagnostic apparatus according to claim 11,
wherein the processor calculates an amount of change in a brightness value in the same region of interest included in time-series data items which are adjacent to each other in the second data group and divides the time-series data items in the second data group into a third data group in which the amount of change in the brightness value is greater than a predetermined value and a fourth data group in which the amount of change in the brightness value is equal to or less than the predetermined value.

14. The ultrasound diagnostic apparatus according to claim 13,
wherein the processor sets filter characteristics such that filter characteristics for the time-series data items in the third data group are different from filter characteristics for the time-series data items in the fourth data group.

15. The ultrasound diagnostic apparatus according to claim 13,
wherein the processor excludes the time-series data items in the fourth data group.

16. The ultrasound diagnostic apparatus according to claim 11,
wherein the processor gives a larger weight to the analysis target data as the correlation coefficient calculated for a plurality of points in the range over the plurality of scanning lines becomes larger, calculates an average value of a correlation matrix in a predetermined range in the range over the plurality of scanning lines, and performs principal component analysis having clutter as a main component, using the average value of the correlation matrix, to remove the clutter component from the analysis target data.

17. The ultrasound diagnostic apparatus according to claim 11,
wherein the processor excludes time-series data items which are continuous in time series and whose number is less than a predetermined number of data items among the time-series data items thus divided.

18. The ultrasound diagnostic apparatus according to claim 1,
wherein the processor excludes time-series data items which are continuous in time series and whose number is less than a predetermined number of data items among a plurality of time-series data items which remain as a result of the exclusion of the time-series data items.

19. The ultrasound diagnostic apparatus according to claim 1,
wherein the processor removes the clutter component from the analysis target data in each division section including a plurality of the analysis target data items divided from the time-series data string, estimates the blood flow information from the plurality of analysis target data items from which the clutter component has been removed in each division section, and combines the blood flow information estimated in a plurality of the division sections.

20. A method for controlling an ultrasound diagnostic apparatus, the method comprising:

repeatedly transmitting an ultrasound beam to a subject a plurality of times in a range over a plurality of scanning lines to acquire a time-series data string of reflected waves from the subject;

estimating an amount of relative positional deviation of a scatterer of the subject which is included in the time-series data string;

excluding time-series data satisfying an exclusion condition based on the estimated amount of positional deviation from the time-series data string to select analysis target data;

removing a clutter component from the selected analysis target data; and analyzing the analysis target data from which the clutter component has been removed to estimate blood flow information of the subject.

* * * * *